United States Patent [19]
Chio

[11] Patent Number: 5,162,991
[45] Date of Patent: * Nov. 10, 1992

[54] TUNING OF A HEART PACEMAKER THROUGH THE USE OF BLOOD PRESSURE AND CARDIOVASCULAR READINGS

[76] Inventor: Shiu-Shin Chio, 4666 Exbury Ct., San Diego, Calif. 92130

[*] Notice: The portion of the term of this patent subsequent to Nov. 14, 2006 has been disclaimed.

[21] Appl. No.: 424,314

[22] PCT Filed: Mar. 8, 1989

[86] PCT No.: PCT/US89/00862
§ 371 Date: Nov. 22, 1989
§ 102(e) Date: Nov. 22, 1989

[87] PCT Pub. No.: WO89/09017
PCT Pub. Date: Oct. 5, 1989

Related U.S. Application Data

[63] Continuation-in-part of Ser. No. 172,660, Mar. 24, 1988, Pat. No. 4,880,013.

[51] Int. Cl.$^5$ ............................................. G06F 15/42
[52] U.S. Cl. ......................... 364/413.03; 128/660.01
[58] Field of Search .............................. 128/660, 695; 564/413.01, 413.03

[56] References Cited

U.S. PATENT DOCUMENTS

| | | | |
|---|---|---|---|
| 3,903,872 | 9/1975 | Link | 128/2.05 A |
| 3,908,639 | 9/1975 | McIntyre | 128/695 |
| 4,009,709 | 3/1977 | Link et al. | 128/2.05 A |
| 4,154,238 | 5/1979 | Link | 128/2.05 A |
| 4,174,707 | 11/1979 | Link et al. | 128/681 |
| 4,271,843 | 6/1981 | Flynn | 128/681 |
| 4,349,034 | 9/1982 | Ramsey, III | 128/681 |
| 4,360,029 | 11/1982 | Ramsey, III | 128/681 |
| 4,367,751 | 1/1983 | Link et al. | 128/682 |
| 4,381,786 | 5/1983 | Duggan | 128/419 |
| 4,427,013 | 1/1984 | Nunn et al. | 128/681 |
| 4,564,020 | 1/1986 | Link | 128/677 |
| 4,587,974 | 5/1986 | Link | 128/685 |
| 4,625,277 | 11/1986 | Pearce et al. | 128/680 X |
| 4,637,400 | 6/1987 | Marcus | 128/653 |
| 4,649,929 | 3/1987 | Weaver et al. | 128/680 |
| 4,651,747 | 3/1987 | Link | 128/677 |
| 4,664,126 | 5/1987 | Link | 128/681 |
| 4,697,596 | 10/1987 | Link | 128/681 |
| 4,699,151 | 10/1987 | Link | 128/681 |
| 4,699,152 | 10/1987 | Link | 128/681 |
| 4,712,563 | 12/1987 | Link | 128/681 |
| 4,727,884 | 3/1988 | Link | 128/681 |
| 4,751,930 | 6/1988 | Terada et al. | 128/681 |
| 4,754,761 | 7/1988 | Ramsey, III et al. | 128/681 X |
| 4,880,013 | 11/1989 | Chio | 128/681 |
| 4,074,711 | 8/1990 | Link et al. | 128/2.05 A |

OTHER PUBLICATIONS

Hadley, H. R. et al. "Experience with a Simplified Computer-Based ICU Monitoring System", 3rd Annual Symposium on Computer Applns. in Med. Care, Oct. 14-17, 1979, Wash. D.C.

L. A. Geddes, "The Indirect Measurement of Mean Blood Pressure in the Horse," The Southwestern Veterinarian, Summer 1970, pp. 289-294.

Feuer, J. M. et al., "The Influence of Cardiac Pacing Mode on the Long-Term Development of Atrial Fibrillation", 38th Scientific Session of American College of Cardiology, Anaheim Calif., Mar. 19-23, 1989.

Primary Examiner—Gail O. Hayes
Attorney, Agent, or Firm—Ice Miller Donadio & Ryan

[57] ABSTRACT

A method is disclosed for determining the blood pressure of a patient. The method includes the steps of affixing a non-invasive pressure inducing device and transducer to the patient. A data stream is obtained from the transducer. The data stream includes pressure data and pulsation signal data. The data stream is processed to create an information stream which coorelates the pressure data and the pulsation signal data. The information stream includes at least two pulse maximum points and at least one pulse minimum point. At least one of the systolic, diastolic and mean arterial pressure of the patient are determined by choosing a pressure determination point in the information stream between the two pulse maximum points. Additionally, an apparatus for determining blood pressure is disclosed.

4 Claims, 16 Drawing Sheets

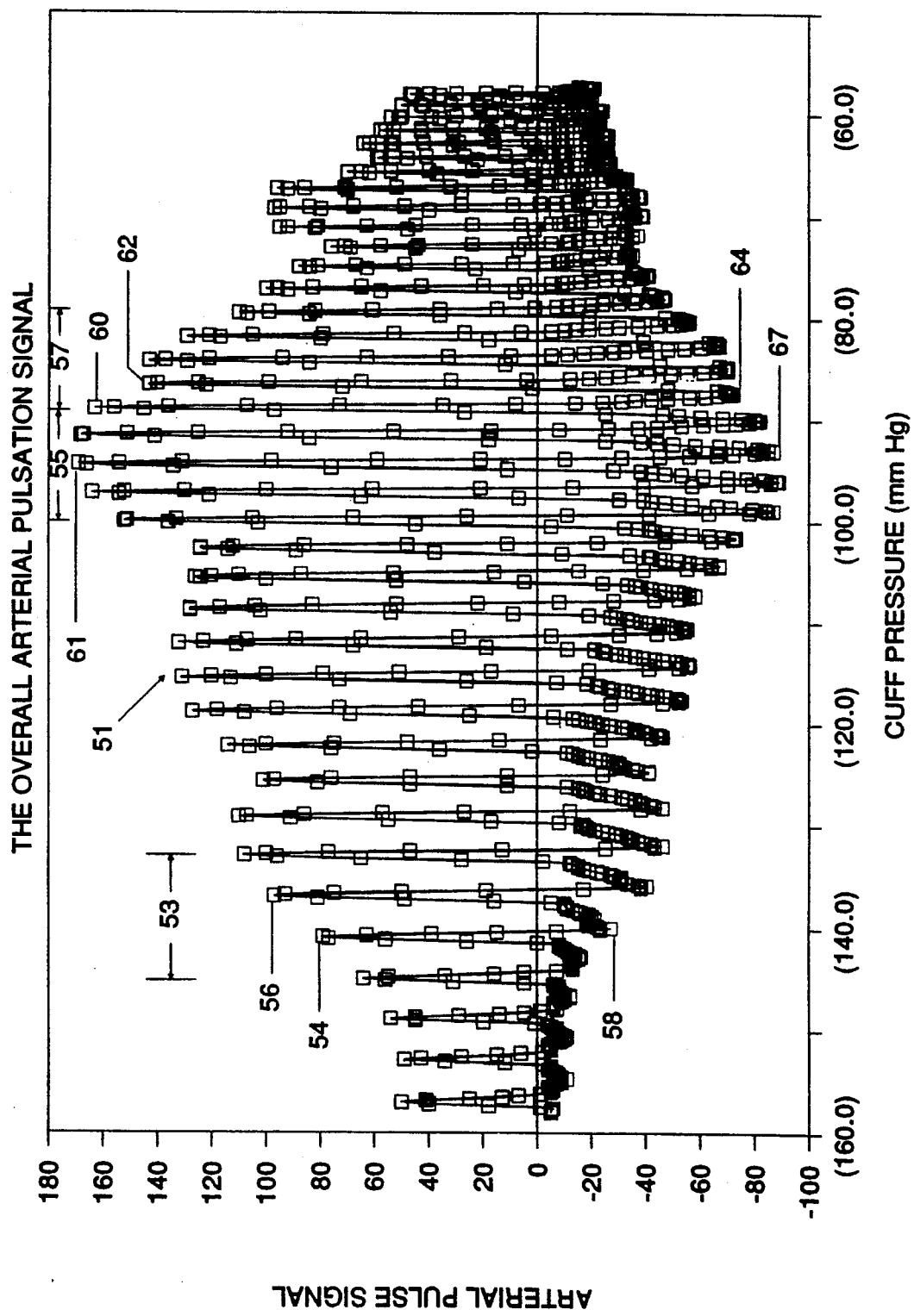

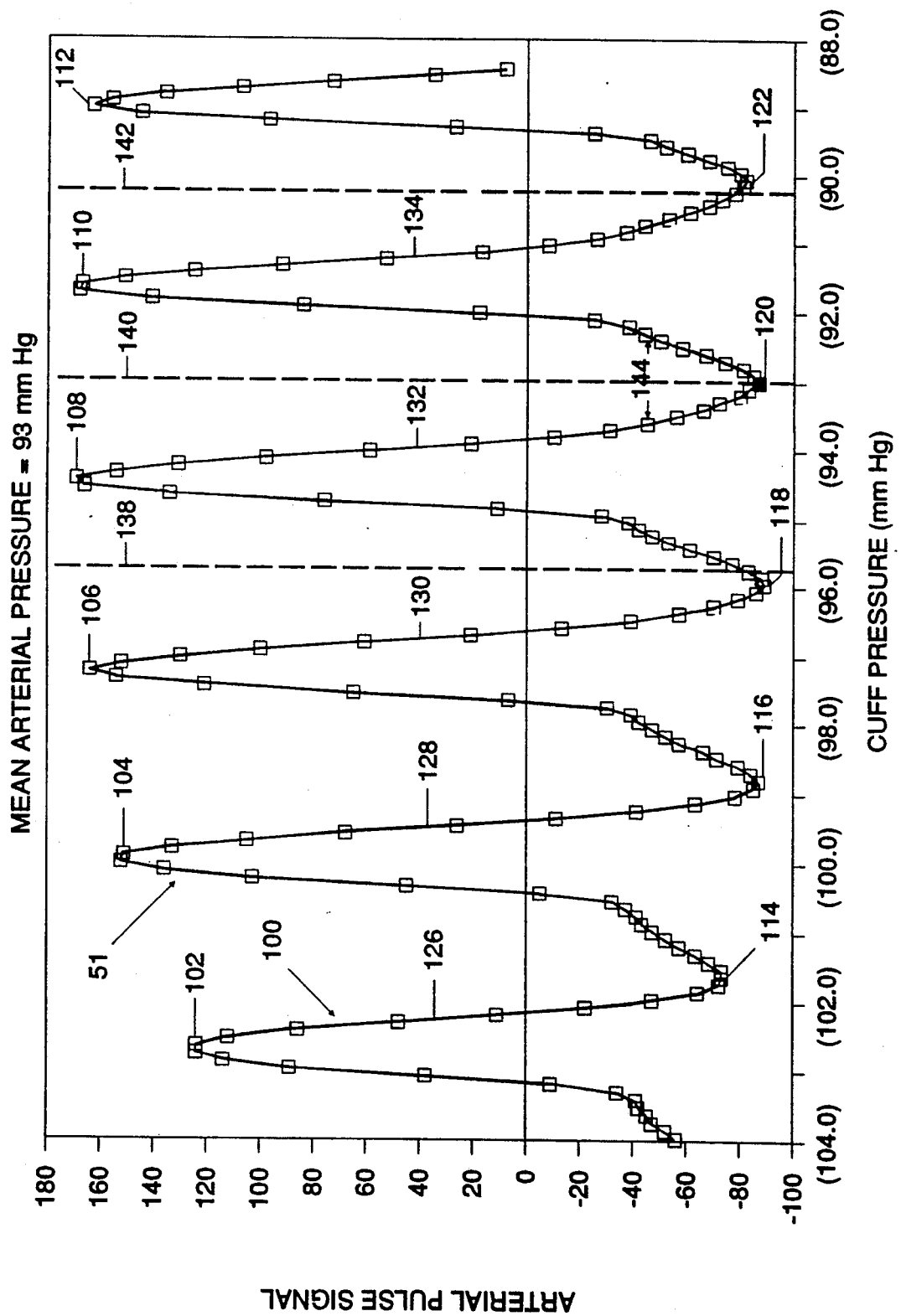

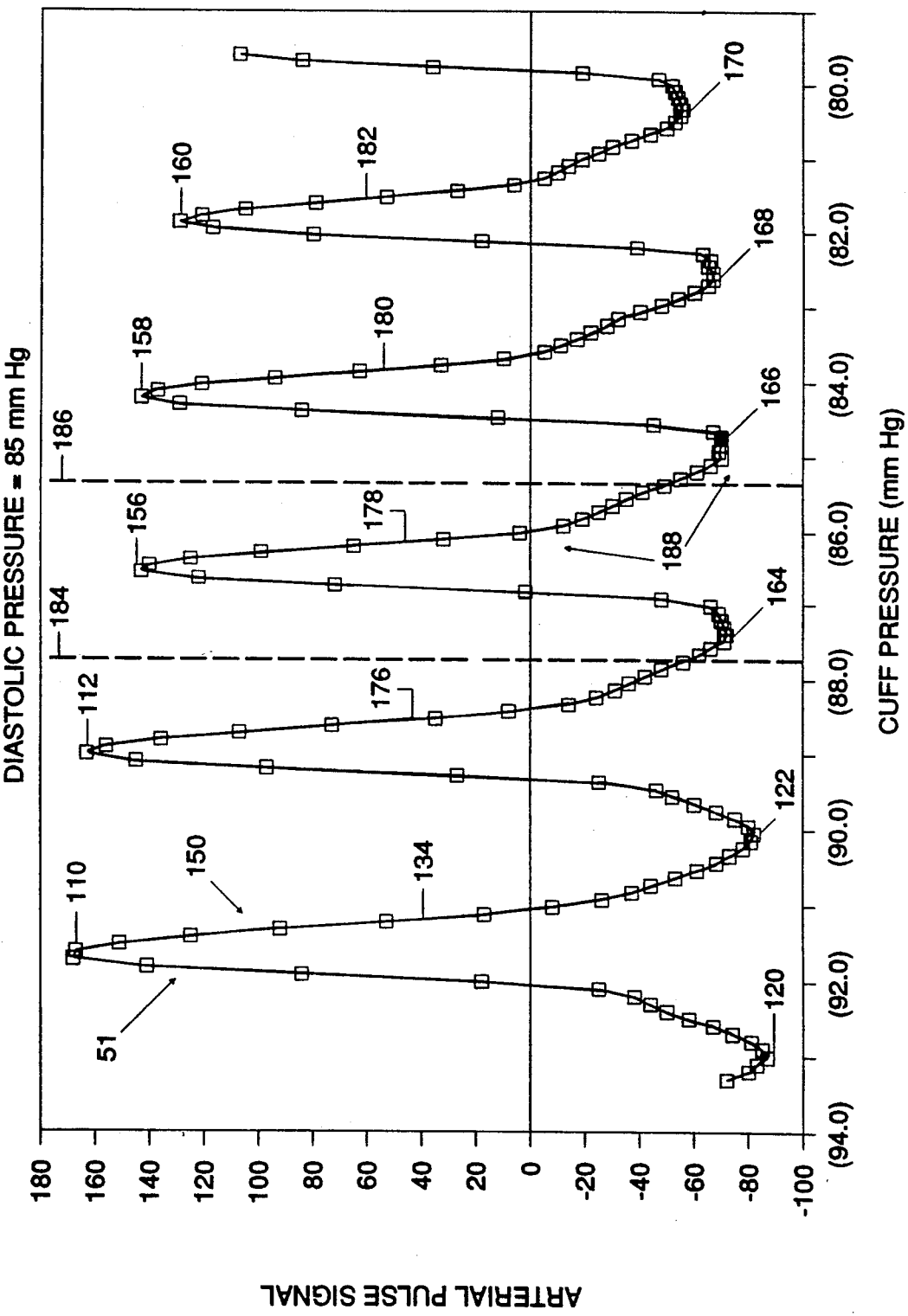

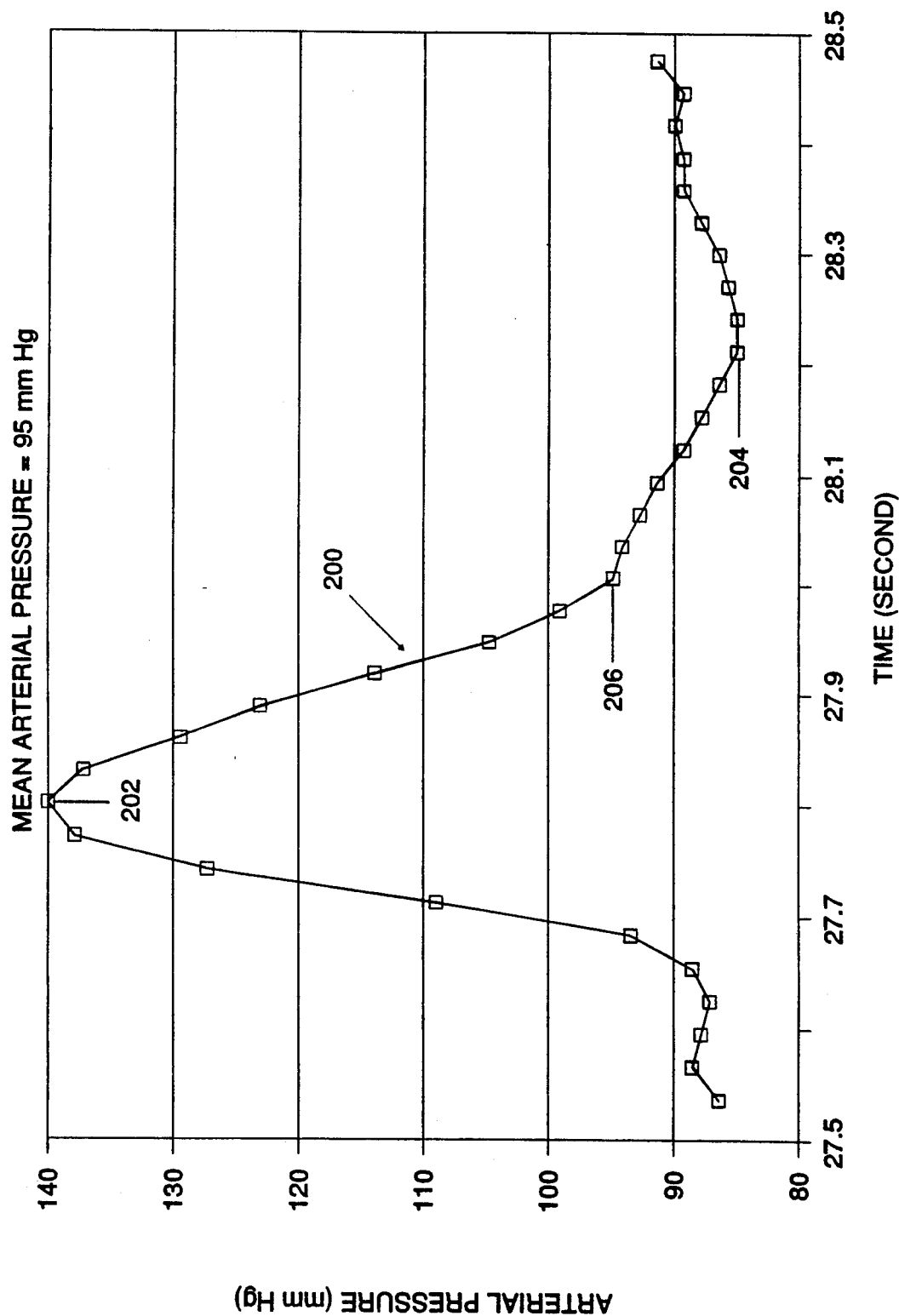

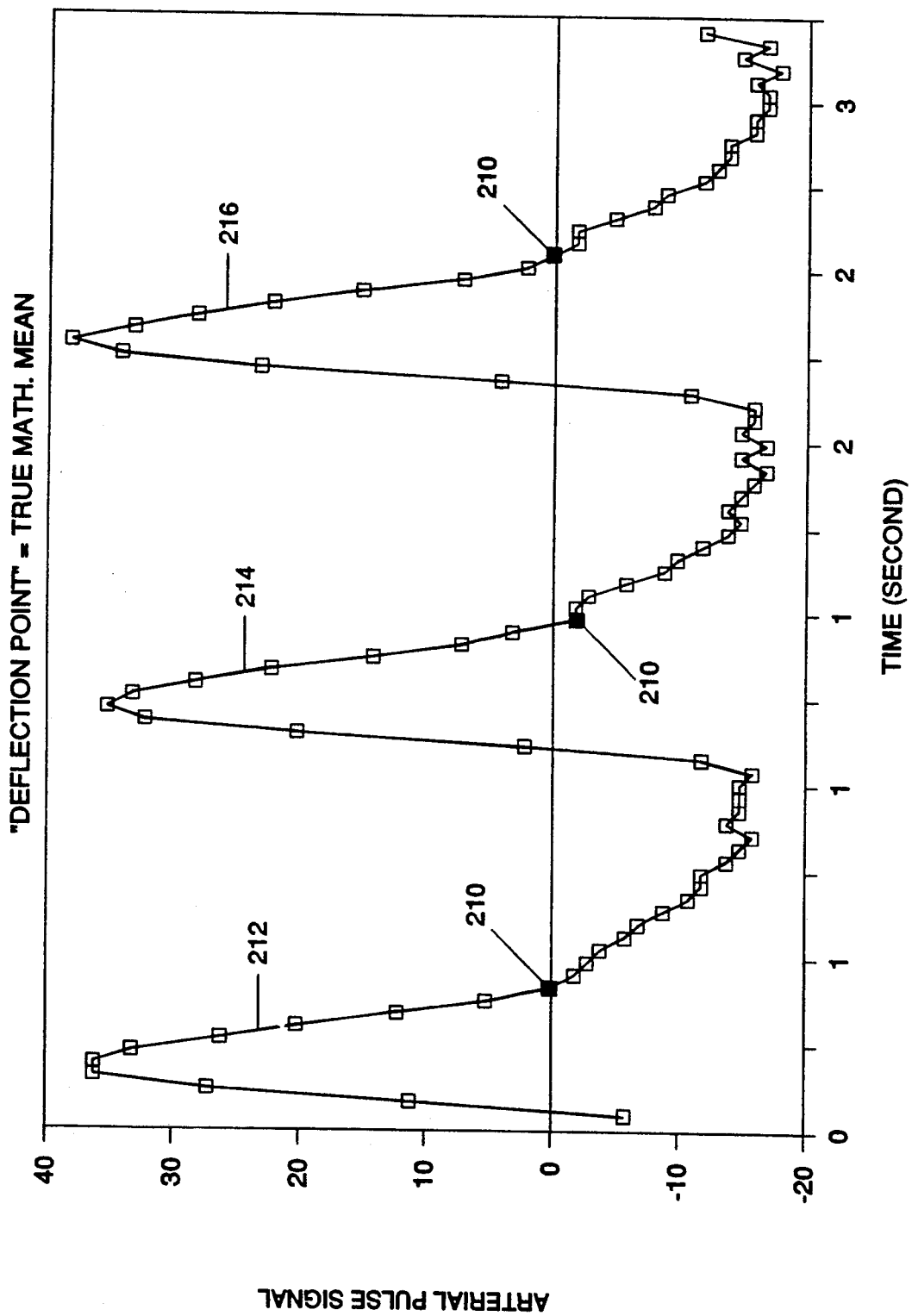

5,162,991

TUNING OF A HEART PACEMAKER THROUGH THE USE OF BLOOD PRESSURE AND CARDIOVASCULAR READINGS

RELATION TO OTHER APPLICATIONS

The instant application claims priority to international (PCT) application number PCT/US89/00826, which was filed on Mar. 8, 1989, and which was published as International Publication No. WO89/09017 on Oct. 5, 1989. The instant application is also a continuation in part of Chio U.S. patent application Ser. No. 07/172/660, filed on Mar. 24, 1988, which has since matured on Nov. 14, 1989 into Chio U.S. Pat. No. 4,880,013. At the time of the filing of the instant application, the instant application was co-pending with the Chio 172,660 application.

TECHNICAL FIELD OF THE INVENTION

The present invention relates generally to a method and apparatus for determining blood pressure and more particularly to a non-invasive method and apparatus for determining blood pressure, tuning a cardiac pacemaker, and for providing the medical practitioner with information about the operation of the cardiovascular system of a patient.

BACKGROUND OF THE INVENTION

One test often performed on patients by medical practitioners is a test to determine the blood pressure of the patient. Blood pressure is tested often because a knowledge of a patient's blood pressure provides an overall reflection of the functioning of his heart and circulatory system.

The blood pressure in a patient's arterial system is represented by the peak systolic and diastolic levels of the pressure pulse and is modified by cardiac output, peripheral arteriolar resistance, distensibility of the arteries, amount of blood in the system, and viscosity of the blood. Accordingly, changes in blood pressure reflect changes in these measurements. For example, the decrease in vessel distensibility in the elderly lowers diastolic pressure and increases systolic pressure to produce systolic hypertension. Increases in blood volume may raise both systolic and diastolic components.

Normal blood pressure in the aorta and large arteries, such as the brachial artery, varies between 100 and 140 millimeters of mercury (mm Hg.) systolic and between 60 and 90 mm Hg. diastolic. Pressure in the smaller arteries is somewhat less, and in the arterioles, where the blood enters the capillaries, it is about 35 mm Hg. However, a wide variation of normal blood pressure exists, and a value may fall outside the normal range in healthy adults The normal range also varies with age, sex and race. For example, a pressure reading of 100/60 may be normal for one person but hypotensive for another Arterial blood pressure can be measured directly or indirectly. The most common known method for measuring blood pressure indirectly is with a sphygmomanometer and stethoscope. The primary benefits of the sphygmomanometer and stethoscope procedure are that it is simple for the medical practitioner to use, is non-invasive and is relatively inexpensive. The sphygmomanometer and stethoscope are often sufficiently inexpensive to make their cost well within the reach of consumers who desire to perform blood pressure tests at home. The primary drawbacks of the use of the sphygmomanometer and stethoscope procedure reside in the limited amount of data that it provides, and the relative inaccuracy of the procedure.

The procedure by which a sphygmomanometer is utilized to determine blood pressure is relatively simple. A collapsed, inflatable blood pressure cuff is affixed snugly and smoothly to a patient's arm, with the distal margin of the cuff at least 3 cm above the antecubital fossa.

Pressure in the cuff is then rapidly increased to a level of about 30 mm Hg above the point at which the palpable pulse disappears. As the cuff is deflated, observations may be made .either by palpation or auscultation. The point at which the pulse can be felt is recorded from the manometer as the palpatry systolic pressure.

The auscultatory method is usually preferred to the technique described above. With this method, vibrations from the artery under pressure, called Korotkoff sounds, are used as indicators.

To determine blood pressure using the auscultatory method, the bell or diaphragm of a stethoscope is pressed lightly over a brachial artery while the cuff is slowly deflated. The pressure reading begin at the time the Korotkoff sounds first become audible. As the cuff is deflated further, the sounds become louder for a brief period The sounds then become muffled and finally disappear The systolic blood pressure is the point at which the Korotkoff off sounds become audible, and the diastolic blood pressure is the point at which the sounds cease to be heard. The traditional manual sphygmomanometer may provide inaccurate blood pressure measurements because it relies too much on human hearing sensitivity and the experience of the operator.

In addition to the "manual" method described above for indirectly measuring blood pressure, several electronic devices exist which measure blood pressure according to the same theory as discussed above One of these devices is the MARSHALL ASTROPULSE 78 Model blood pressure measuring device which is manufactured by the Marshall Medical Corporation of Lincolnshire, Ill.

One problem with the electronic devices discussed above is that they do not provide very accurate measurements of blood pressure Electronic devices may not be able to measure all patient's blood pressure accurately because electronic devices usually depend upon some preassumed signal conditions for determining blood pressure For example, female patients typically have a thicker fat layer than male patients. This thicker fat layer can lead to a less accurate blood pressure measurement in female patients.

Another difficulty encountered with the above-described indirect blood pressure measurement techniques is that they only provide a rather limited amount of information. Specifically, they do not provide significant information relating to the dynamics of the cardiovascular system of the patient, such as information relating to the volume of blood flowing through the cardiovascular system and the operation of the valves of the heart Another method for measuring blood pressure is by a direct measurement technique. In a direct measurement of arterial blood pressure, a needle or catheter is inserted into the brachial, radial, or femoral artery of the patient. A plastic tube filled with heparinized saline solution connects the catheter to a pressure sensitive device or a strain-gauge transducer. The mechanical energy that the blood exerts on the transducer's recording membrane is converted into changes in electrical voltage or current that can be calibrated in millimeters of mercury. The electrical signal can then be transmitted to an electronic recorder and an oscilloscope, which continually records and displays the pressure waves.

This direct measurement technique is more accurate than the indirect sphygmomanometer method, and yields an electrically integrated mean pressure. However, as will be appreciated, the direct measurement technique has several drawbacks. The invasive nature of the technique makes it more difficult for the practitioner, as well as less convenient, and more traumatic for the patient.

One other method for indirectly measuring blood pressure is disclosed in Geddes, et al., "The Indirect Measurement of Mean Blood Pressure in the Horse," *THE SOUTHWESTERN VETERINARIAN*, Summer, 1970, p. 289-294. The Geddes article describes the indirect measurement of blood pressure through the oscillometric method.

The oscillometric method is concerned with the amplitude of the oscillations communicated to a cuff encircling a body member containing a suitably large artery. During deflation of the cuff from above systolic pressure, a sequence of oscillations of the cuff-pressure indicator can be seen. At suprasystolic pressure, small oscillations in cuff pressure are evident. When cuff pressure falls just below systolic pressure, the amplitude of the oscillations increases. With continued deflation of the cuff, the oscillations grow in amplitude, reach a maximum, and then decrease continually until the cuff pressure drops below the diastolic pressure of the patient. Currently, several digital-display electronic blood pressure monitors are commercially available which utilize the oscillometric method. One such commercially available device is the NORELCO brand Model HC-3001 home use blood pressure measuring device which is manufactured by the North American Phillips Corporation of Stamford, Conn.

The Geddes article also discusses the measurement of mean arterial pressure (MAP) MAP is defined as the average pressure that pushes blood through the circulatory system in the human body. True MAP is not arithmetic average of systolic and diastolic pressure, but rather depends on the height and contour of the arterial pressure wave. True MAP is dependent upon a patient's Cardiac Output (CO) and the Total Peripheral Resistance (TPR) of the patient's cardiovascular system. Due to this relation, the equation

MAP=(CO) (TPR)

is often used by medical practitioners to describe MAP.

MAP is believed by many practitioners to be the most important measurement of blood flow through the circulatory system. It is essential for a practitioner to know the patient's MAP when deciding whether to prescribe medicines for the patient to control hypertension. For a further discussion of MAP determinations, see the Geddes article.

The device described in Geddes consists of a battery operated electronic oscillometer which displays cuff pressure and the oscillations in cuff pressure. Within the device is a pressure transducer, an amplifier and a rapidly responding meter which displays only the amplitude of the oscillations in cuff pressure. A gain control is provided to adjust the amplitude of the display of the oscillations. Additionally, an auxiliary output jack is provided to permit the oscillations to be recorded on a graphic recorder. Geddes utilized the oscillometer discussed above simultaneously with a direct pressure measuring device on the same animal at the same time to compare the accuracy of his indirect measurements with the direct measurements. Geddes found that his indirect oscillation method was not as accurate as the direct method, with the average ratio of indirect to direct pressure being about 0.92:1.

Another indirect method and apparatus for measuring blood pressure is described in Ramsey U.S. Pat. Nos. 4,360,029 and 4,349,034. The '029 and '034 patents are related, and disclose generally identical subject matter.

The Ramsey patents relate to an automatic indirect blood pressure reading method and apparatus which automatically and adaptively pump up an arm cuff. The cuff is pumped to a proper pressure by taking the previous cuff pressure measurement and adding approximately 60 mm to the old pressure before beginning measurement of the amplitude of the oscillations in the cuff Once the amplitude of oscillations at the starting pressure are measured, the cuff is deflated a determined pressure increment to a lower pressure The oscillations at this lower cuff pressure are then measured.

Ramsey requires that the pressure oscillations satisfy a plurality of artifact detecting tests before a peak oscillation measurement is accepted as valid. Should an artifact be detected, additional oscillations are measured until the oscillations test free of artifacts When this integrity test is satisfied or some predetermined time interval is exceeded, the cuff is once again deflated a pressure increment. The apparatus continues in this fashion until maximum amplitude oscillations are obtained at the lowest cuff pressure, which is indicative of the mean arterial pressure Notwithstanding the above discussed advances in the indirect measurement of blood pressure, room for improvement exists It is therefore one object of the present invention to provide a method and apparatus for measuring blood pressure which provides the medical practitioner with a more accurate method of measuring blood pressure, and which provides the practitioner with information regarding the cardiovascular system beyond that of mere systolic and diastolic arterial pressures.

SUMMARY OF THE INVENTION

In accordance with one aspect of the present invention, a method is provided for determining blood pressure of a patient. The method comprises the steps of affixing a non-invasive pressure inducing means and transducer means to the patient. A data stream is obtained from the transducer means. The data stream includes pressure data and pulsation signal data. The data stream is processed to create an information stream which correlates the pressure data and the pulsation signal-- data. The information stream includes at least two systolic maximum points and at least one diastolic minimum point. At least one of the systolic, diastolic and mean arterial pressures of the patient are determined by choosing a pressure determination point in the information stream between the two systolic maximum points.

Preferably, the method also includes the steps of providing a graphic display means and graphically displaying the information stream.

In accordance with another aspect of the present invention, a method is provided for determining mean arterial blood pressure of a patient. The method comprises the steps of affixing a non-invasive pressure inducing means and a transducer means to the patient. A data stream is obtained from the transducer means. The data stream includes pulsation signal data. The data stream is processed to create an information stream which includes pulsation signal data and time data. The patient's systolic and diastolic pressures are determined. A pressure determination point is chosen in the information stream. The chosen pressure determination point is then utilized along with the determined systolic and diastolic pressures to determine the patient's mean arterial pressure.

In accordance with a third aspect of the present invention, an apparatus is provided for determining blood pressure of a patient The apparatus comprises a noninvasive pressure inducing means and a transducer means which are attachable to the patient for providing a data stream including a pressure data and pulsation signal data. Processing means are provided for processing the data to create an information stream which correlates the pressure data and the pulsation signal data. A graphic display means is provided for graphically displaying the information stream so created.

One feature of the present invention is that an information stream comprised of pressure data and pulsation data is provided. From this information stream, an instantaneous point is chosen for determining the patient's systolic blood pressure, diastolic blood pressure or mean arterial pressure. This feature of using an "instantaneous point" has the advantage of enabling the medical practitioner to determine diastolic, and systolic blood pressures and mean arterial pressures more accurately than known, prior non-invasive blood pressure determining techniques.

Another feature of the present invention is that the apparatus of the present invention utilizes a non-invasive pressure determining means, such as a cuff pressure sleeve, sphygmomanometer and transducer. This feature has the advantage of making the blood pressure determination process more convenient for the medical practitioner and less risky for the patient than invasive pressure determining techniques.

It is also a feature of a preferred embodiment of the present invention that a graphic display means is provided for graphically displaying the information stream, and a data storage means is provided for storing the information stream. The graphic display feature has the advantage of providing the medical practitioner with valuable data about the operation of the heart and circulatory system, such as the operation of the valves in the heart. The storage feature has the advantage of promoting a proper diagnosis of the patient's condition by enabling the medical practitioner to compare the current condition of the patient's heart and circulatory system against a prior, stored set of data showing the conditions of the patient's heart at an earlier date. Through an evaluation of the differences between the prior and current information streams, the medical practitioner can better analyze the current condition of the patient's heart and better determine whether there is any improvement or deterioration in the patient's condition.

A further feature of the present invention is that it provides two methods for determining Mean Arterial Pressure. These two methods are referred to herein as "the midpoint method" and the "mathematical calculation method."

It was found by the applicant that both the midpoint method and the mathematical calculation method have the advantage of providing more consistent MAP results than the maximum pulse amplitude method, which is described in the Geddes article. The midpoint method of the present invention determines the patient's MAP by utilizing the cuff pressure, below the systolic pressure, when the pulse cycle minimum reaches the midpoint on the cuff pressure axis between two consecutive arterial pulse signal maximum points. The midpoint method has the advantage of not requiring the medical practitioner to predetermine the patient's systolic and diastolic pressures. The midpoint method is well-suited for use in routine blood pressure monitoring situations and in situations wherein a numerical, electronic readout device having limited memory and computing capability is employed.

The mathematical calculation method comprises a computation of the mean of a patient's pulsation wave form data. To utilize the mathematical calculation method of the present invention, a pressure determination point is chosen at a cuff pressure below the patient's diastolic pressure. To choose a pressure determination point, a point is chosen in the information stream between a systolic maximum and a diastolic minimum, wherein the rate of change of the cuff pressure data versus pulse signal data changes significantly. The above described point is chosen as a "deflection point." The deflection point is chosen as a point at which to mathematically calculate MAP because this deflection point represents the point at which the patient's aortic valve is closed, and thus represents the intrinsic blood pressure at the point wherein the aortic valve is closed. The point wherein the aortic valve is closed is chosen because it is at this point that the patient experiences the most long lasting and significant "push" of blood through his circulatory system.

The mathematical calculation method has several advantages over the midpoint method. One advantage is that the mathematical calculation method is less sensitive to low frequency noises, such as breathing noises and body movement noises These low frequency noises can interfere with the accuracy of the results of the test. Further, the mathematical calculation method can be utilized with cuffless blood pressure measuring devices.

When the mathematical calculation method is used with cuff devices, the results are less affected by the design and stability of the cuff. Additionally, the mathematical calculation method provides generally more consistent and accurate results than the midpoint method Because of the enhanced consistency and accuracy of the mathematical calculation method, it is particularly well suited to situations such as surgical procedures requiring highly accurate and consistent information. The mathematical calculation method does have some disadvantages (when compared to the midpoint method) in that the mathematical calculation method generally requires the use of a device having greater memory and computing capabilities Additional features and advantages of the present invention will become apparent to those skilled in the art upon consideration of the following detailed description of a preferred embodiment exemplifying the best mode of carrying out the invention as presently perceived.

BRIEF DESCRIPTION OF THE DRAWINGS

FIG. 2 is a sample graphic display of the information stream produced by the instant invention showing the invention in its first mode displaying overall arterial pulse data as a function of cuff pressure;

FIG. 4 is a graphic display, similar to FIG. 3, showing pulse signal as a function of cuff pressure in the mean arterial pressure range;

FIG. 5 is a graphic display, similar to FIGS. 3 and 4, showing pulse signal as a function of cuff pressure in the diastolic pressure range;

FIG. 6 is a graphic display showing information processed according to the present invention in its third mode, wherein a pulse signal of a single cycle is displayed as a function of time, wherein the maximum point of the pulse is assigned to equal the systolic pressure (as determined from FIG. 3) and the minimum point of the pulse is assigned to equal the diastolic pressure (as determined from FIG. 4) to illustrate the existence of the deflection point between the pulse maximum and the pulse minimum of the pulse cycle;

FIG. 6b is an expanded view of a portion of FIG. 6a;

Figure 11:
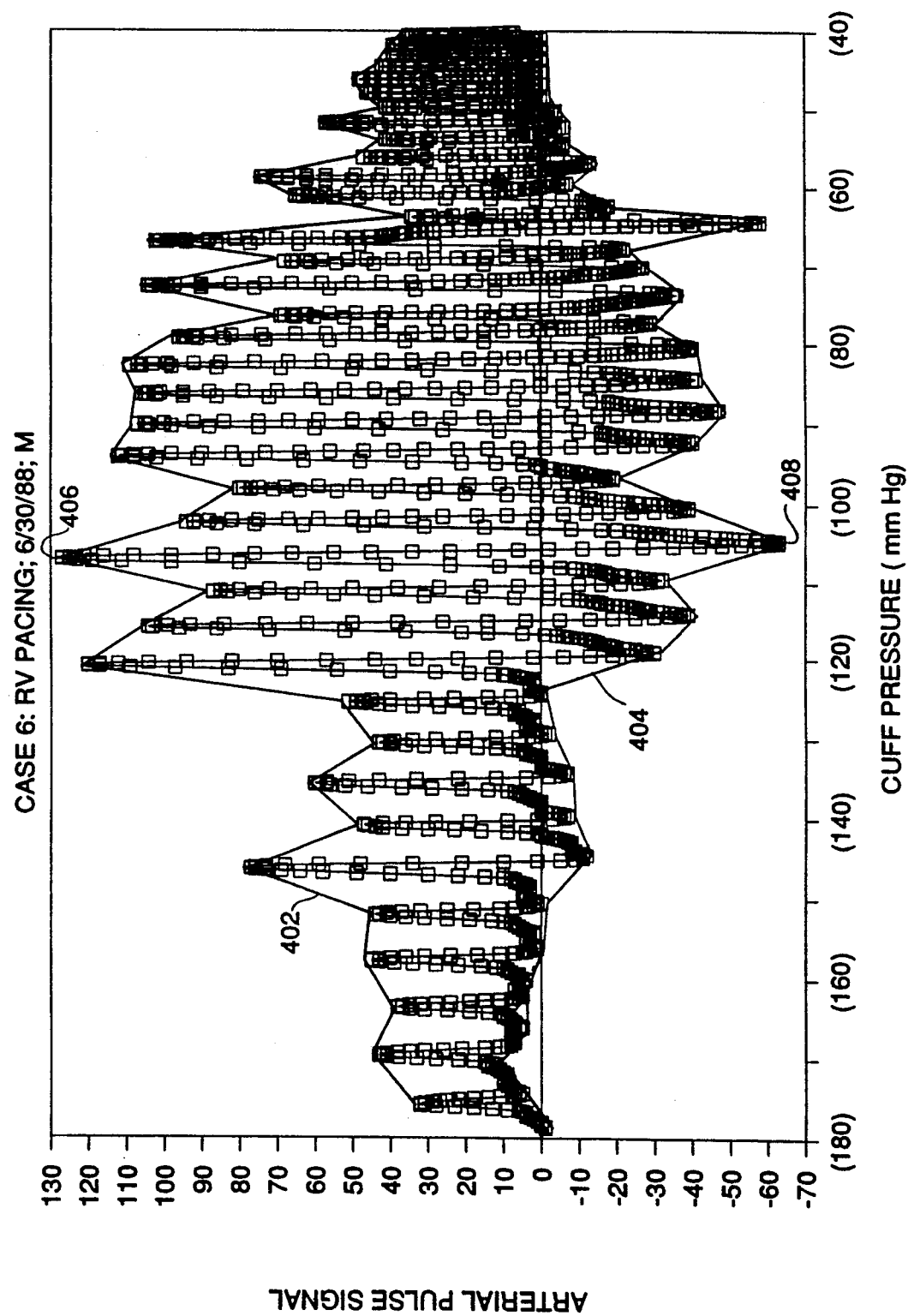
Figure 12:
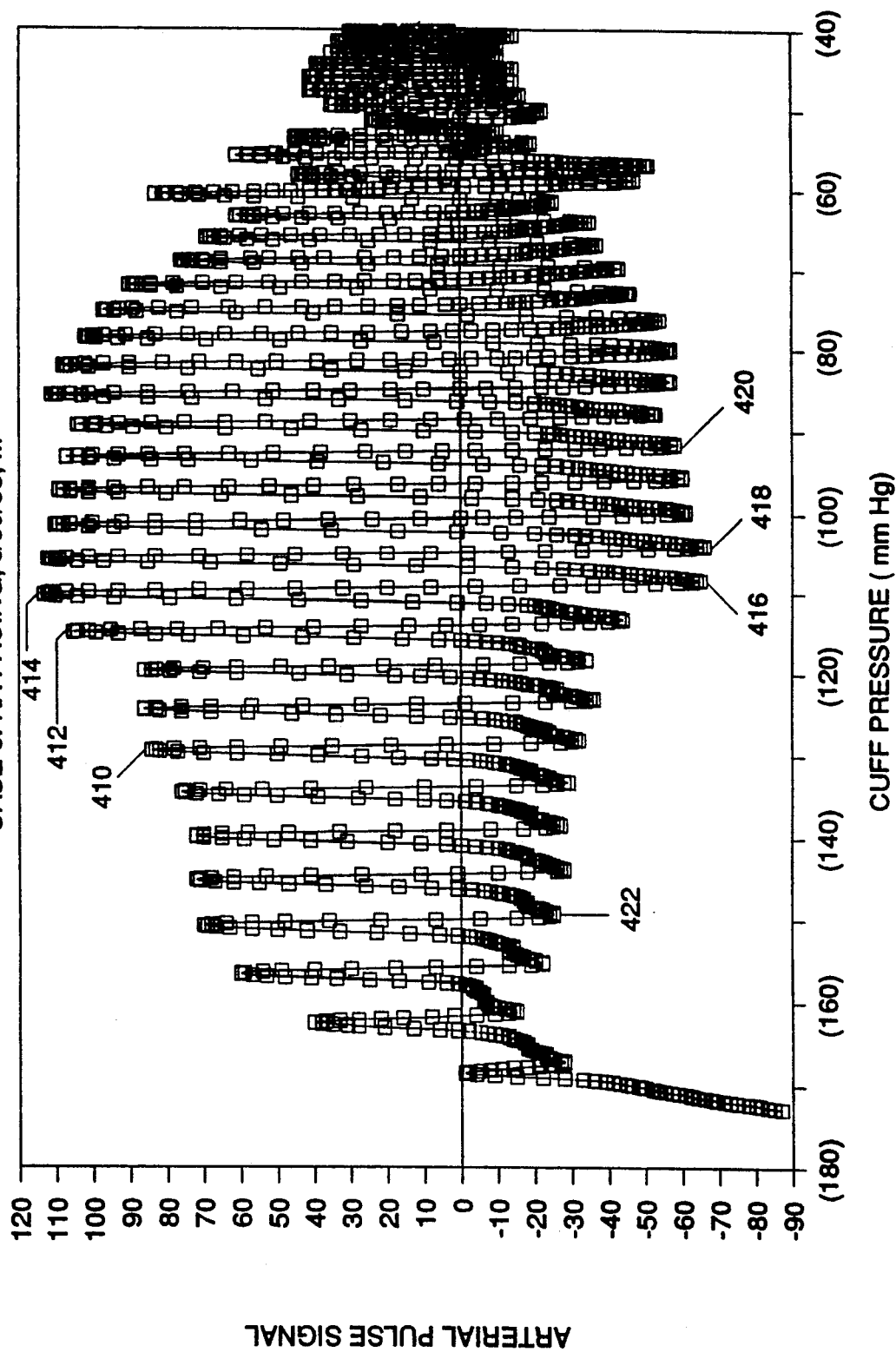

Figures numbered 9 and 10 are omitted intentionally;

FIG. 11 a graphic display similar to FIG. 2, displaying overall arterial pulse data as a function of cuff pressure for a patient having a pacemaker installed, but not tuned properly;

FIG. 12 is a graphic display similar to FIG. 11: and

Figure 13:
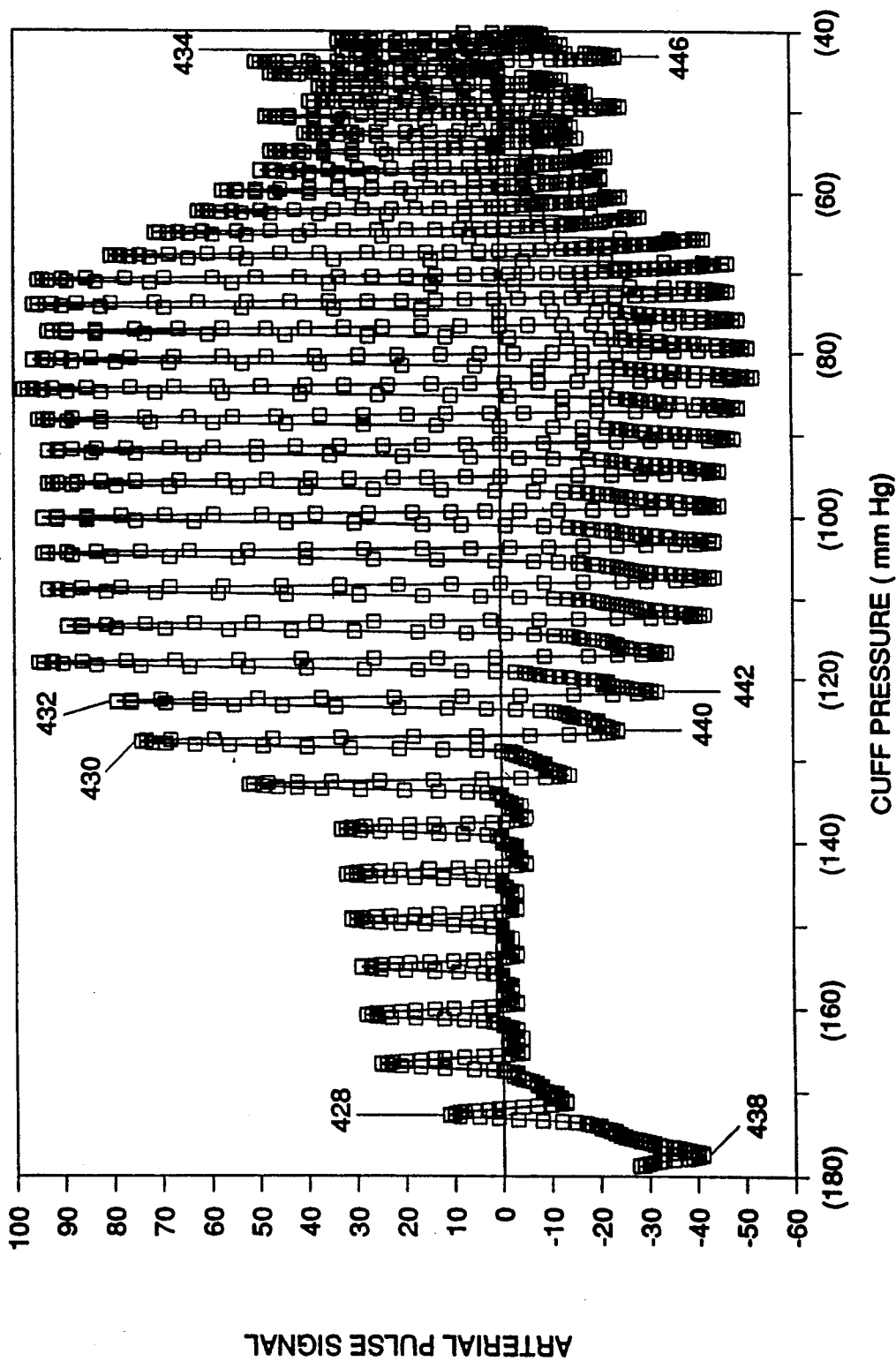

FIG. 13 is a graphic display similar to FIG. 11 wherein the patient's pacemaker is tuned properly.

DETAILED DESCRIPTION OF THE DRAWINGS

A. Components

Figure 1:
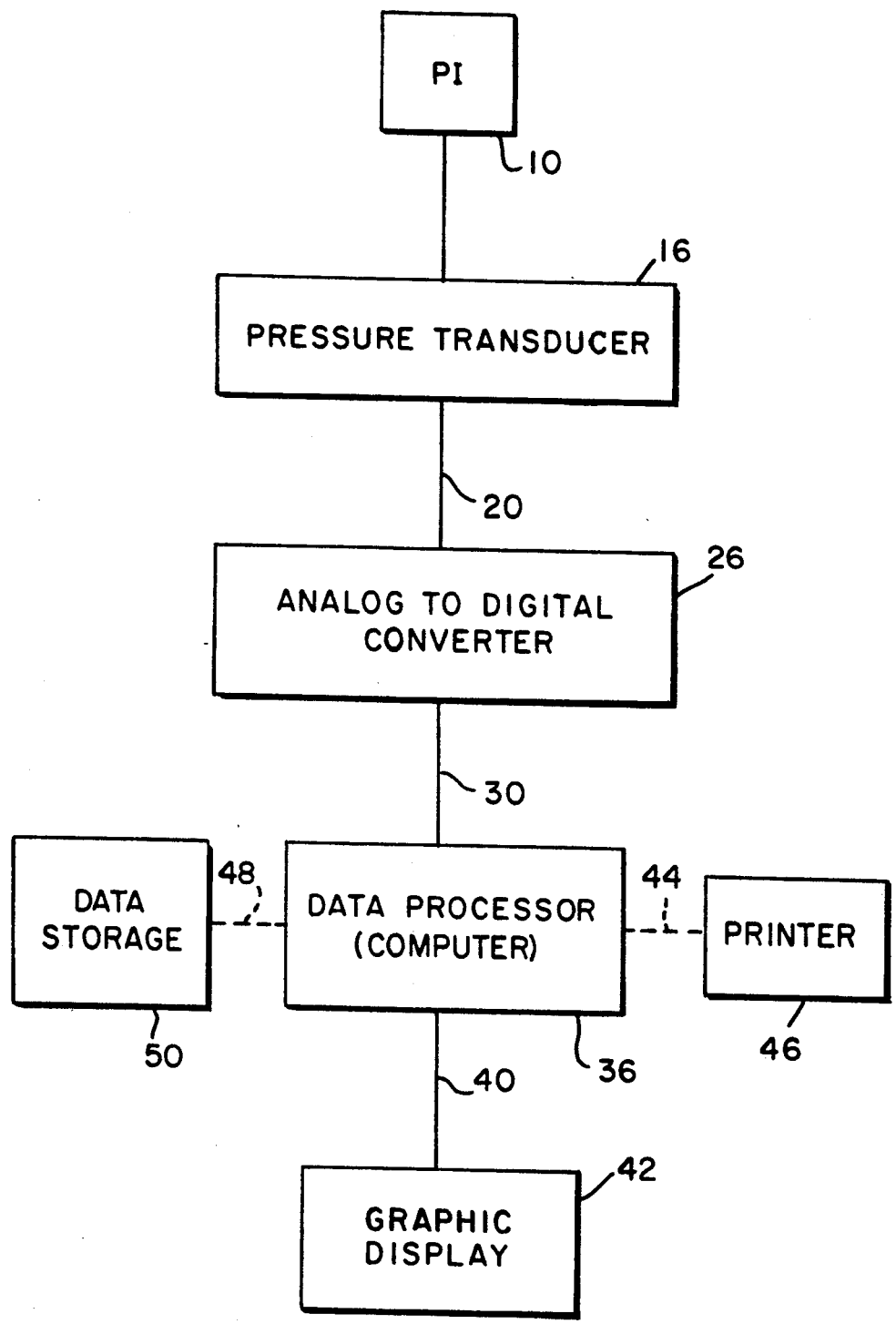
FIG. 1 is a diagrammatic representation illustrating the components utilized in the instant invention.

FIG. 1 presents a block diagram illustrating the components which comprise the apparatus of the present invention, and which are utilized in conjunction with the method of the present invention The apparatus of the present invention includes a noninvasive pressure inducing means such as cuff 10 for exerting a pressure on a body part, such as the arm. A transducer means 16 is provided for picking up the total pressure, including the background pressure and the small oscillation (pulsation) signals. Typically, the background pressure signals are picked up as DC signals, and the pulsation signals are picked up as AC signals The background pressure signals and pulsation pickup up are those signals induced by the cuff 10.

Figure 1A:
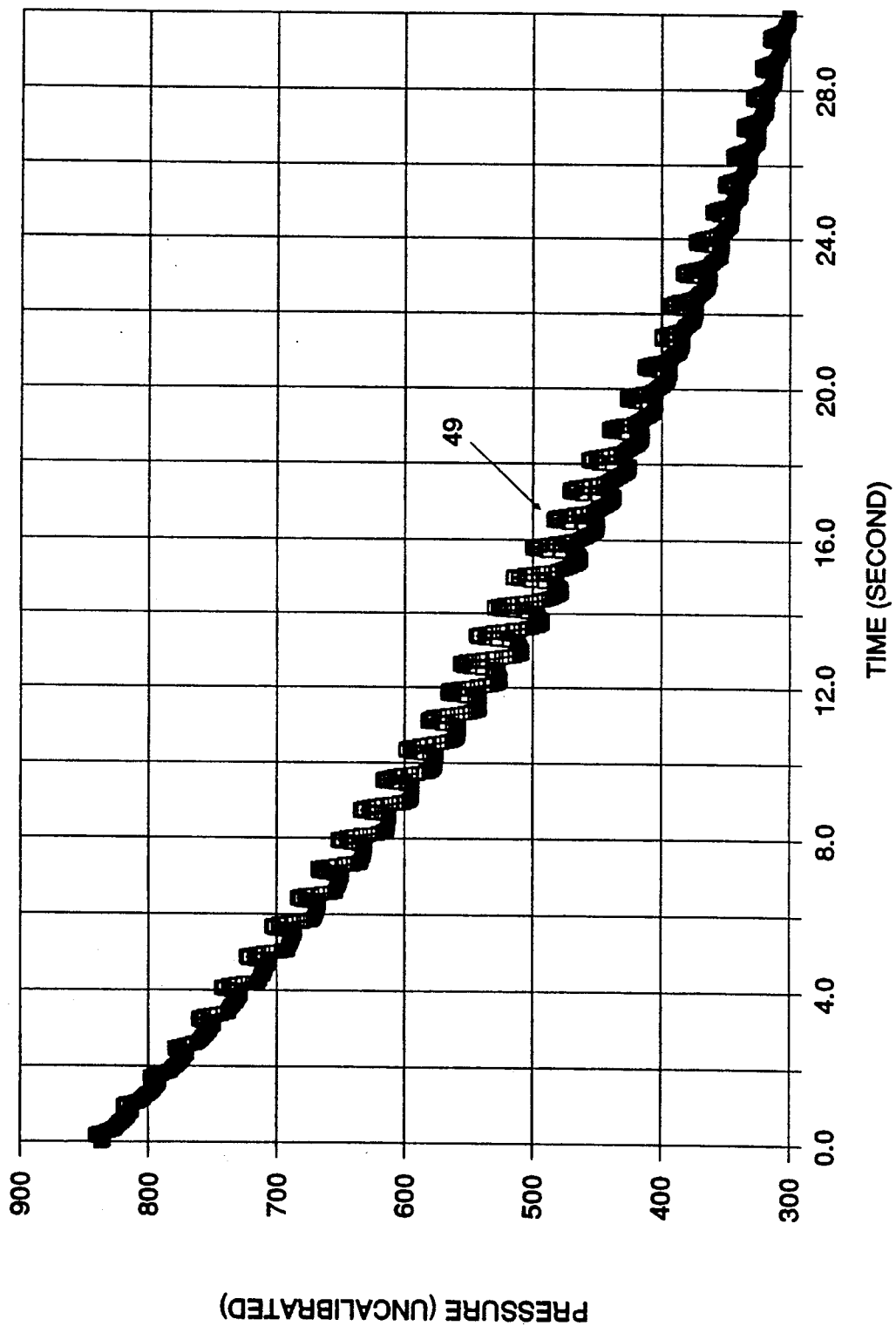
FIG. 1a is a sample graphic display of the information stream produced by the instant invention, displaying cuff pressure (uncalibrated) as a function of time.

The transducer means 16 converts these signals so picked up into an electrical signal A graphic display of the data stream which results from these signals is shown in FIG. 1a.

Although a wide variety of pressure inducing means can be used, the pressure inducing means preferably comprises an inflatable cuff 10 which can be wrapped around a limb of a patient Typically, such an inflatable cuff 10 includes a pump means (either manually activated or electronically activated) which pumps air into the interior of the cuff 10 to exert pressure on the body part An example of such a cuff 10 is the cuff supplied with the Norelco blood pressure monitor Model No HC-3001 cuff which is manufactured by the North American Phillips Corporation of Stamford, Conn.

Additionally, most, commercially available cuffs provided as a part of an oscillometric blood pressure monitoring system can be utilized in conjunction with the present invention, so long as a compatible adaptor is utilized to connect the cuff 10 to the pressure transducer means 16. Further, with more extensive modification, cuffs designed for use with non-oscillometric blood pressure monitoring devices can also be utilized with the present invention.

Preferably, the cuff 10 should include a pressure stop valve which permits the user to maintain a selected, constant pressure in the 20 to 200 mm Hg. pressure range. The stop valve feature is useful in that it permits the user to obtain arterial pulse wave forms, and thereby extract additional information about the patient's cardiovascular condition. Examples of such arterial wave forms are shown in FIGS. 7, 7a, 8 and 8a, and will be discussed in more detail below.

The pressure transducer 16 primarily comprises a solid state pressure sensor or similar device which is capable of picking up pressure signals, and converting these pressure signals into an analog electrical signal for transmission from the transducer means 16. An example of a commercially available transducer which can operate in conjunction with the present invention is the pressure transducer supplied with the Norelco blood pressure monitor, Model No. HC-3001, discussed above Preferably, the pressure transducer 16 will have a linear response rate, or will have a known correlation between the input pressure received by the transducer 16 and the output electrical signal (e.g. voltage) sent out by the transducer 16. The linear response or known correlation characteristics facilitate the calibration of the transducer 16 against a standard pressure gauge, such as a mercury pressure gauge. Additionally, the transducer 16 should have a fast response rate and a wide frequency response. Preferably, the response rate should be less than or equal to 0.001 second, and the frequency of the response rate should be between about 0.2 hertz and 50 hertz or higher. It has been found by the applicant that a fast response rate and a wide frequency response contribute to an accurate determination of the systolic and diastolic blood pressure, and the means arterial pressure The transducer 16 generates a voltage signal which comprises a generally continuous overall pressure data stream 20. The overall pressure data stream 20 is sent in a generally continuous manner to the analog to digital convertor 26. The analog to digital convertor 26 converts the analog information provided by the transducer 16 into digital information. The analog to digital convertor 26 should preferably have a sampling rate of 4,000 samples per second or higher; a resolution of 12 bits or better; more than one channel for other multipurpose applications; and the capability to convert digital signals to analog signals for feedback control.

Although the above mentioned qualities are preferred, they may not be necessary since the bit resolution and sampling rate of the final data acquired depends largely on the software program utilized in conjunction with the present invention. Generally, a combination of a software package and an analog to digital convertor 26 that will provide final data acquisition of better than 100 items of data per second is adequate for the present invention. However, better digitizing resolution in the data stream 20 is always preferable. An example of an analog to digital convertor which will perform the functions necessary for the instant invention is the Eight Channel, High Speed analog to digital convertor, Model No. DAS-8, which is manufactured by the MetraByte Corporation of Taunton, Mass.

A digitized pressure data stream 30 is fed from the analog to digital convertor 26 to a data processing means such as computer 36. As with data stream 20, the digitized data stream 30 represents an essentially continuous data stream. The computer 36 should preferably have a fast clock speed (e.g. 4.7 megahertz or faster); a large enough memory to store the data (e.g. 256 kilobytes or greater); and an easy disk operation system, such as the IBM DOS operation system.

It should also be noted that the computing speed and memory size required for performing the tasks of the present invention depend on the particular software chosen. Thus, with the proper software, the user might be able to utilize a computer 36 having a smaller memory and a slower clock speed. Generally, a clock speed (e.g., 10,000 Hz) fast enough to achieve a final data acquisition rate of better than 100 data bits per second is adequate for the present invention. Further, a memory of less than 256 kilobytes can be utilized if a graphic program is used which is more simple than the LOTUS 1-2-3 program utilized in conjunction with the present invention.

Examples of computers 36 having sufficient clock speed and memory to perform the functions necessary in the instant invention include the IBM Model PC, PC/XT, and PC/AT computers manufactured by the IBM Corporation, and their compatible equivalents. Examples of such compatible equivalents can be found in most computer related magazines.

As will be appreciated, the computers 36 described above will not process the information of the data stream 20 without proper software to perform the processing The software utilized in conjunction with the present invention should perform several functions.

The first function performed by the software is to control the analog to digital convertor 26, so that the digitized data stream 30 can be received by the computer 36. A second function performed by the software is to convert the digitalized data system 30 into ASC II format and store the data in a data storage means such as a disk 50 so that the data can be retrieved by a program such as LOTUS 1-2-3 for further data processing and graphic display. A third function of the software is to receive and to input total time This inputting of total time starts the converting performed by the analog to digital convertor 26 at time zero on the computer's 36 internal clock, and ends the analog to digital converting when the total time is up.

A fourth function performed by the software is to filter out the AC oscillation component of digitized data stream 30, so that a DC pressure curve of the cuff pressure and a separate AC pulsation stream are obtained. This step need not be performed by the software, as a hardware filter can be employed to separate the AC and DC components of the pressure signal obtained from the pressure transducer 16 before the data stream 20 is fed to the analog to digital converter 26.

A fifth function of the software is to calibrate the DC cuff pressure curve by utilizing a pre-calibrated factor. This pre-calibrated factor is a number obtained by comparing the digitized number from the analog to digital convertor 26 to either a standard pressure gauge reading or to the digital reading of a digital blood pressure monitoring device which is utilized simultaneously in conjunction with the present invention. The sixth function performed by the software is to perform various necessary mathematical calculations, such as integration, derivation, etc.

The software utilized by the applicant in conjunction with the present invention comprises a two component software package. The first component comprises a translation component, and the second component comprises a data manipulation and graphic display component.

The translation program comprises a data acquisition program, written by the applicant to collect data from the data stream 30, and to store the data in a data storage device such as a disk 50 or hard drive (not shown). The translation component collects the data and translates it into a form usable by the data manipulation/graphic display component so that the data manipulation/graphic display component can manipulate the data into a usable form and display it graphically. The functions performed by the translation program are (1) noise filtering to filter out spike noises, (2) fitting the curve to the data points obtained, and (3) calibrating the pressure data to millimeters of Mercury. One example of a commercially available translation program which can perform the functions necessary to perform in the present invention is the LAB TECH NOTEBOOK data acquisition software program Model LTN-03, manufactured by the MetraByte Corporation of Taunton, Mass.

The data manipulation/graphic display component is a data base program which re-manipulates the data and graphically displays the data on a graphic display means 42. An example of a data manipulation/graphic display program which functions in conjunction with the present invention is LOTUS 1-2-3 manufactured by LOTUS Development Corporation of Cambridge, Mass.

The data processing means 36 feeds a generally continuous information stream 40 to a graphic display means, such as a video system 42 for the computer 36. Alternately, an information stream 44 can be fed to a printer 46 to construct a permanent record of the information contained in the information stream 44. As will be appreciated, printer 46 also comprises a graphic display means. Preferably, the printer 46 used should be either a dot-matrix printer or a laser printer having the capability to display the information stream 44 graphically.

As another alternative, an information stream 48 can be fed to a data storage means, such as a disk 50 or a hard drive for storage and later retrieval. Through the use of the data storage means to store the data produced by the patient, the medical practitioner can be provided with access to current and historical data about the patient.

Although information streams 40, 44, 48 are given three separate designating numbers, it will be appreciated that information streams 40, 44, 48 all contain essentially the same information.

B. Procedure to Operate the Invention

The following procedure is employed in conjunction with the present invention. The cuff 10, is affixed to the patient and operated in accordance with its usual operating procedures. A generally continuous overall pressure data stream 20 is derived from the cuff 10 and transducer 16, respectively, and fed into the analog to digital convertor 26. The analog to digital convertor 26 converts the analog information of the pressure data stream 20 into a digitalized pressure data stream 30.

The digitized information contained in the data streams 30, 32 is then processed by the computer 36 to separate the AC component (the pulsation signal) from the overall pressure data stream 30 received by the computer 36. Further, the computer 36 calibrates the cuff pressure data into units of millimeters of mercury to then create the information streams 40, 44, 48, wherein pulsation signal and cuff pressure are correlated to give pulsation signal as a function of cuff pressure. Additionally, pulsation signal and time are correlated to give the pulsation signal as a function of time.

The information in the information streams 40, 44, 48 is then fed respectively to the video screen 42, printer 46, or disk 50. From the data so displayed, the systolic, diastolic and mean arterial pressures of the patient can be determined along with other information about the cardiovascular system of the patient.

A sample graphic display is shown in FIG. 1a which displays the information stream 40, 44, 48 produced by the present invention, wherein cuff pressure (uncalibrated) is shown as a function of time. The curve 49 of FIG. 1a is relevant in that it shows that during the test, the pressure exerted by cuff 10 is decreased smoothly over time. It will be appreciated by those skilled in the art that the cuff pressure at the beginning of a blood pressure test should be greater than the patient's estimated systolic pressure, and the cuff pressure at the end of the test should be less than the patient's diastolic pressure.

FIG. 1a is also relevant in that it shows that the duration of the test was thirty seconds, and that the rate of decrease of cuff pressure was generally constant during the test. Although the applicant employed a 30 second test, a shorter or longer test period could be utilized. The use of a shorter test period would have the advantage of reducing the test time the patient would need to endure, but would have the disadvantage of reducing the accuracy of the test due to the fewer number of collected data points. A longer test would have the advantage of increasing the accuracy of the test due to the larger number of data points collected. However, the larger number of data points would likely delay the response time of the computer 36, and could overload the computer's 36 ability to handle the data.

A generally smooth decrease in cuff pressure during the test is preferred as it facilitates the construction and interpretation of the graphic displays produced by the instant invention. However, in some circumstances it may be preferable to decrease the pressure non-linearly.

There are several different manners in which the cuff pressure data, pulsation signal data and the time data so correlated can be processed, depending on the user's preference, and on the information so desired. Presented below are several examples of "modes of operation," along with an explanation of the information produced by these various modes, the uses to which the modes are put, and the value of each mode in diagnosing the condition of the patient.

C. Modes of Operation

1. First Mode.

A graphic display is shown in FIG. 2 which illustrates the operation of the invention in its first mode. In this first mode, a curve 51 is shown wherein the patient's pulse signal is displayed as a function of cuff pressure. FIG. 2 displays the pulse signal/cuff pressure curve 51 throughout the entire duration of the test, which, in the present example is thirty seconds. The long time period displayed in this first mode is useful to the practitioner in that it helps the practitioner to determine whether any irregularities exist in the patient's pulse signal. For example, the display will show whether the patient missed a pulse signal, and whether the patient's pulse signals are spaced irregularly. A missed pulse signal or irregular spacing of the patient's pulse signals may indicate that the patient's heart has a serious functional problem.

Curve 51 includes three primary regions: the systolic region 53, the mean arterial region 55, and the diastolic region 57. Although the boundaries of these regions cannot be defined with absolute precision, some generalizations can be made. The systolic region 53 comprises that portion of curve 51 wherein the arterial pulse signal first begins to rise. In curve 51, the systolic region 53 includes the area around apex points 54 and 56. The mean arterial region 55 includes the area of curve 51 adjacent to the peak arterial pulse signal, which in curve 51 is the portion of curve 51 adjacent to apex point 68.

The diastolic region 57 includes the region wherein the arterial pulse signal decreases rapidly, and in curve 51 includes the portion of curve 51 adjacent to apex points 60, 62. Portions of the systolic region 53, the mean arterial region 55 and the diastolic region 57 of curve 51 are shown in more detail in FIGS. 4, 5, and 6, respectively.

The display of the first mode also provides the practitioner with a quick determination of the patient's systolic pressure, diastolic pressure and mean arterial pressure. The systolic pressure is determined from the display in the following manner. It will be noted that a sharp rise in the arterial pulse signal occurs between apex point 54 and apex point 56. To determine the systolic pressure, one utilizes the nadir point 58 between apex points 54 and 56. One then reads the cuff pressure at nadir point 58 to obtain a quick estimate of the patient's systolic pressure. In the instant example, the cuff pressure at nadir point 58 is approximately 140 mm Hg.

To determine the diastolic pressure, one utilizes the portion of the curve 51 where the arterial pulse signal is decreasing. One then looks for apex points, such as apex points 60, 62 wherein a relatively large decrease in the arterial pulse signal occurs. The nadir point 64 between apex point 60, 62 is chosen, and the cuff pressure at the nadir point 64 is utilized as the diastolic pressure. In the instant example, the diastolic pressure of the patient at nadir point 64 is approximately 87 mm Hg.

To determine an estimate of the patient's mean arterial pressure from the graph of FIG. 2, one utilizes the nadir point 67 following the highest apex point 68 displayed on the graph. One then reads the cuff pressure at this nadir point 67 to obtain an estimate of the patient's mean arterial pressure, which, in the instant example is about 93 mm. Hg.

2. The Second Mode.

Figure 3:
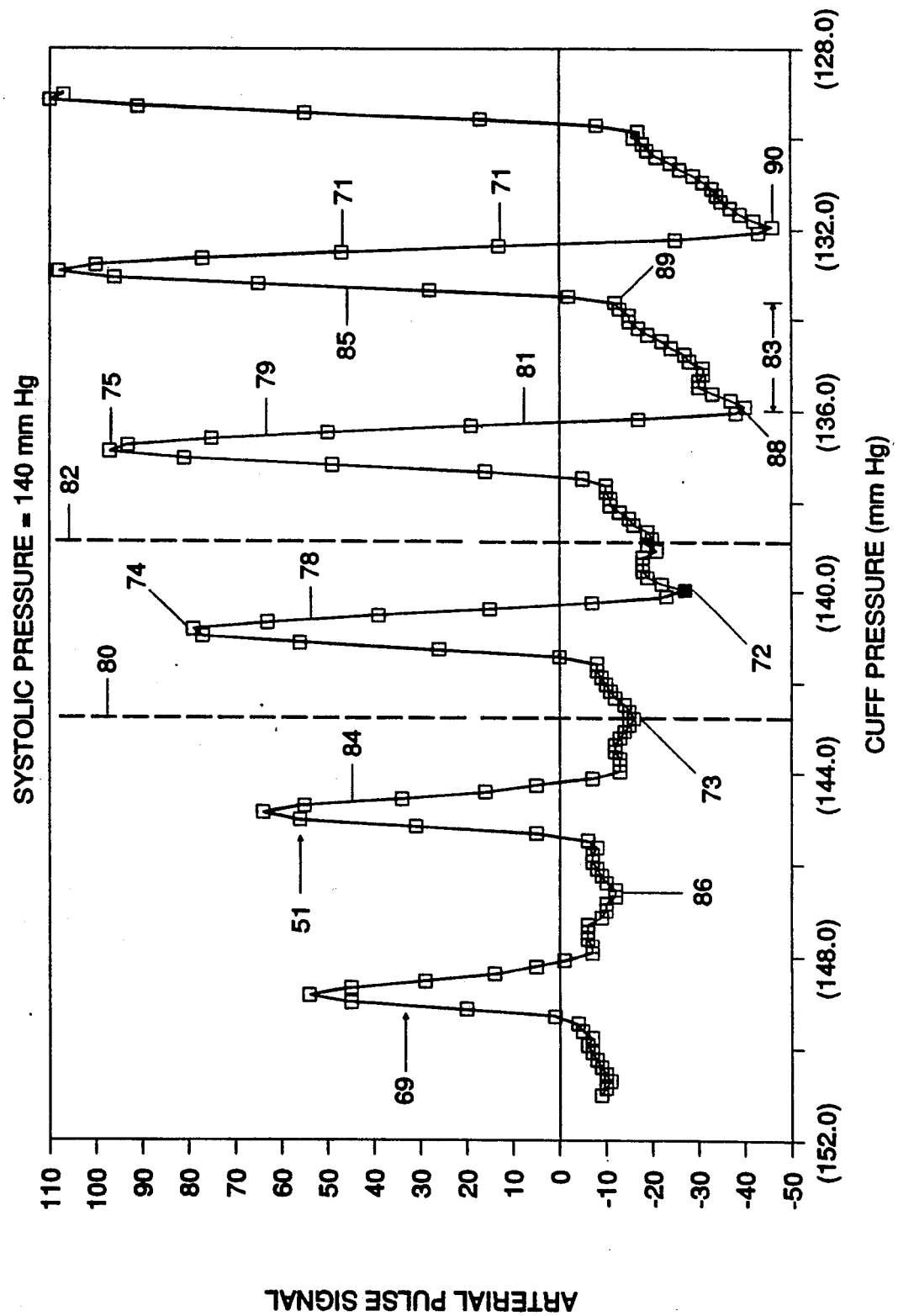
FIG. 3 is a sample graphic display showing the information stream processed according to the second mode of the invention, displaying pulse signal as a function of cuff pressure in the systolic pressure range.

A graphic display of the information streams 40, 44, 48 obtained through the operation of the present invention in its second mode is shown in FIGS. 3, 4 and 5. More particularly, FIG. 3 displays an information stream wherein the arterial pulse signal is shown as a function of cuff pressure in the systolic range of the patient; FIG. 4 displays an information stream showing the arterial pulse signal as a function of cuff pressure in the mean arterial range; and FIG. 5 displays the arterial pulse signal as a function of cuff pressure in the diastolic pressure range.

The determination of the systolic pressure of the patient according to the present invention will now be explained with reference to FIG. 3. It will be noted that FIG. 3 comprises a graphic display of a portion 69 of curve 51 of the generally continuous information stream. The curve portion 69 includes a series of data points such as data points 71, which are separated in time generally by 0.037 second. These data points 71 include a series of nadir points, such as nadir points 72, 73, and a series of apex points, such as apex points 74, 75. Apex points 74, 75, relate to pulse cycle (systolic) maxima in a particular pulse cycle, and the nadir points 72, 73 represent pulse cycle minimum points. For purposes of this discussion, a pulse cycle is defined as a segment of the curve portion 69 between any two apex points, such as the third cycle 78, which includes that part of the curve portion 69 between apex point 74 and apex point 75. It should also be noted that each cycle, such as fourth cycle 79, includes three portions: a rapidly descending portion 81, a trough portion 83 and a rapidly ascending portion 85. The rapidly descending portion 81 of each cycle is the interval of the cycle wherein the arterial pulse signal decreases rapidly relative to the change in cuff pressure The rapidly descending portion 81 is characterized by a wide spacing between points, and in fourth cycle 79 includes the interval between apex point 75 and nadir point 88. The trough portion 83 of each cycle is the interval of the cycle wherein the change of arterial pulse signal relative to the change in cuff pressure is generally less than in either the rapidly descending portion 81 or the rapidly ascending portion 85 The trough portion 83 is characterized by relatively close spacing of the data points, and in the fourth cycle 79 includes the interval between nadir point 88 and data point 89. The rapidly ascending portion 85 of each cycle is the interval of each cycle wherein the arterial pulse signal increases rapidly relative to the change in cuff pressure Similar to rapidly descending portion 81, rapidly ascending portion 85 is characterized by wide spacing between data points. In fourth cycle 79, the rapidly ascending portion 85 is the interval of cycle 79 between data point 89 and apex point 91.

A pressure determination point is chosen from curve portion 69. The cuff pressure at this pressure determination point comprises the systolic pressure of the patient. In curve portion 69 the pressure determination point is the nadir point 72 of the third cycle 78. Nadir point 72 is chosen as the pressure determination point because it meets the following three criteria.

The first criteria met by nadir point 72 is that nadir point 72 comprises the nadir point between the apex points 74, 75 wherein a large rise occurs in the arterial pulse signals at the apex points (or systolic maxima).

A second criteria for choosing nadir point 72 is that it comprises the nadir point in the cycle 78, wherein a substantial decrease occurs in the arterial pulse signals between nadir points 72, 73 of adjacent cycles.

The third criteria for choosing nadir point 72 relates to the relative position of nadir point 72 in pulse cycle 78. If one were to draw imaginary bisector lines, such as bisectors 80, 82 which intersect the cuff pressure axis, and which bisect the respective second cycle 84 and third cycle 78, one would notice that the nadir point 73 of second cycle 84 is positioned generally adjacent to, or on bisector 80. However, it will also be noticed that nadir point 72 of the third cycle 78 is positioned to the left of bisector 82 and, in fact, is positioned at the extreme left of the trough portion 83 of the curve portion 69 in third cycle 78. In choosing a nadir point to serve as a pressure determining point, one chooses the nadir point 72 of the first cycle (here third cycle 78) wherein the nadir point 72 is located at or close to the beginning of the trough portion 83.

By way of contrast, it should be noted that nadir points 86, 73 of the first and second cycle 84, respectively, are located near the center of the trough portion, and the nadir points 88, 90 of the fourth and fifth cycles are located in a position similar to nadir point 72 at the extreme beginning or left end of the trough portion of the respective fourth and fifth cycles.

Using nadir point 72 as the pressure determination point, one can determine that the systolic pressure of the patient is 140.0 mm Hg. by reading the cuff pressure at the nadir point 72.

The choice of nadir point 72 has physiological significance. Nadir point 72 represents a point on the curve 51 wherein the pulse signal drops to its minimum almost immediately following its prior peak at apex point 74. This immediate drop in the pulse signal indicates that the interval of time between peak 74 and nadir point 72 represents the time at which the patients blood pressure overcomes the pressure of the cuff 10 to thereby permit a small amount of blood to flow through the arteries blocked by the cuff 10. This small amount of blood flow causes the sudden drop in the arterial pulse signal. This sudden drop is reflected in the graph by the positioning of nadir point 72 at the beginning of the trough portion of cycle 78, and is also reflected by the drop in arterial pulse signal between adjacent nadir points 73, 72.

The present invention provides a more accurate means for determining systolic pressure. As will be appreciated by medical practitioners, an accurate knowledge of a patient's systolic blood pressure is extremely useful in diagnosing a patient's condition. One reason the knowledge of systolic pressure is important is that practitioners often utilize a systolic pressure exceeding 140 mm Hg. as a bench mark for determining whether a patient is hypertensive.

Determining systolic pressure accurately is not an easy task. A patient's systolic pressure is the highest pressure point of the cardiovascular system. Difficulty arises in determining systolic pressure since this highest point may only remain for a short period of time, for example, 0.1 second or less. Due to the short duration of this highest point, the actual highest point systolic pressure may be missed by a practitioner or a device measuring systolic pressure, because the practitioner or device are incapable of capturing the systolic pressure at its highest point.

The present invention overcomes many of these problems by better identifying the very point at which the patient's blood pressure reaches this highest point systolic pressure. By better identifying this highest point systolic pressure, the present invention provides generally more consistent data than that provided by known prior art electronic devices.

A graphic display illustrating a patient's arterial pulse signal as a function of cuff pressure is shown in FIG. 4. Specifically, FIG. 4 displays the patient's arterial pulse signal and cuff pressure in the range wherein the patient's mean arterial pressure can be calculated utilizing the "min-point method" discussed above.

FIG. 4 is similar to FIG. 3 in that it displays a generally sinusoidal portion 100 of curve 51 comprised of a generally continuous series of data points separated in time by about 0.037 seconds. Curve portion 100 is taken from the mean arterial range 55 of curve 51 and includes a series of apex points 102, 104, 106, 108, 110, 112 and a series of nadir points 114, 116, 118, 120, 122. The apex points 102, 104, 106, 108, 110, 112 and nadir points 114, 116, 118, 120, 122 define a series of five pulse cycles, including a first cycle 126, second cycle 128, third cycle 130, fourth cycle 132, and fifth cycle 134. For purposes of illustration, imaginary bisectors 138, 140, 142 have been drawn through the respective third cycle 130, fourth cycle 132, and fifth cycle 134.

It has been found by the applicant that the patient's mean arterial pressure (MAP) can be determined by reading the cuff pressure from the graph of the nadir point 120 of the cycle 132 wherein the nadir point 120 is positioned at the middle of the trough portion 144 of the cycle 132. To clarify this, it should be noted that nadir point 120 intercepts bisector 140 of the fourth cycle 132. Further, the nadir point 118 of the prior cycle (third cycle 130) falls to the left of bisector 138 and the nadir point 122 of the succeeding cycle (fifth cycle 134) falls to the right of bisector 142. When one reads the cuff pressure at nadir point 120, one finds that the patient's mean arterial pressure is approximately 93 mm Hg.

It should be noted that the mean arterial pressure determined from FIG. 4 (93 mm Hg) is essentially the same as the mean arterial pressure (94 mm Hg) estimated from FIG. 2, wherein the maximum amplitude point method was utilized. One advantage to the use of the mid-point method over the maximum amplitude method is that the mid-point method is generally not as sensitive to extraneous noises and the maximum amplitude method. The mid-point method is not as sensitive to noises for many of the same reasons that an FM radio signal is normally less noisy than an AM radio signal.

Although the mid-point method of the present invention does provide an advance over the maximum amplitude method, the mathematical calculation method is likely more accurate than the mid-point method. The mathematical calculation method is likely more accurate because it is less affected by the patient breathing deeply, the interposition of a sleeve between the cuff 10 and the body part, and the presence of a significant fat layer between the arteries and skin layer of the patient. The mathematical calculation method is discussed below as the third mode of the present invention.

A graphic display is presented in FIG. 5 which demonstrates the determination of a patient's diastolic blood pressure according to the present invention. FIG. 5 displays a generally sinusoidal curve portion 150 of curve 51, which is comprised of a series of data points separated in time by about 0.037 second. Curve portion 150 overlaps with curve portion 100 (FIG. 4) insofar as both curve portions 100, 150 share two apex points 110, 112, two nadir points 120, 122 and cycle 134. Curve portion 150 also includes apex points 156, 158, 160 and nadir points 164, 166, 168, 170. These apex points 110, 112, 156, 158, 160 are nadir points 122, 164, 166, 168, 170 define five pulse cycles 134, 176, 178, 180, 182. Bisectors 184, 186 have been drawn through cycles 176 and 178, respectively, in a manner similar to the bisectors 80, 82 of FIG. 3 and the bisectors 138, 140, 142 of FIG. 4.

To choose a pressure determination point, one chooses a nadir point 166 and reads the cuff pressure (85 mm Hg.) at the pressure determining nadir point 166. To determine which nadir point to use as the pressure determination point, one uses the nadir point 166 which is located at, or adjacent to the end of the trough portion 188 of its respective cycle. As will be noted from the graph, nadir points 164, 168, 170 are generally not disposed adjacent to the end of their respective trough portions. As discussed in connection with FIG. 4, nadir point 120 is directly in the middle of the trough portion of its respective pulse cycle.

Another way of viewing pressure determining nadir point 166 is that nadir point 166 is at or adjacent to the beginning the portion of cycle 178 wherein the arterial pulse signal rises rapidly toward the successive apex point 158. The choice of a nadir point 166 which is disposed at, or near the beginning of the rapidly ascending portion of a cycle as a pressure determining point has physiological significance. A nadir point 166 so positioned indicates that the pressure exerted by the cuff 10 is sufficiently insignificant so that the cuff 10 no longer restricts the flow of blood through the arteries. As will be familiar to medical practitioners, a patient's diastolic pressure is generally defined as the pressure at which the pressure exerted by a cuff 10 no longer restricts the flow of blood.

The applicant found that utilizing this method provides a rather consistent and accurate determination of a patient's diastolic blood pressure. It is believed by applicant that the reason for this enhanced consistency and accuracy of the present invention is due to the fact that the present invention better captures the exact arterial pulse signal point wherein the pressure exerted by the cuff 10 no longer restricts the flow of blood past the cuff 10. Additionally the accuracy and consistency of the method of the present invention are enhanced because the present invention is less affected by external noises that can affect the amplification of pulses.

3. Third Mode.

A graphic display of the blood pressure determination method of the present invention in its third mode is shown in FIG. 6. The third mode is utilized to determine a patient's mean arterial pressure according to the "mathematical calculation method" of the present invention. The graphic display in FIG. 6 shows a single pulse cycle having a plurality of data points connected together to form a generally sinusoidal curve 200. Curve 200 correlates the arterial pressure of the patient as a function of time, with arterial pressure being displayed on the Y axis, and time being displayed on the X axis. Although cuff pressure is not shown in curve 200, the cuff pressure responding a curve 200 is a cuff pressure lower than the patient's measured diastolic pressure. The reasons for choosing a cuff pressure less than diastolic pressure will be explained in more detail below.

The graphic display shown in FIG. 6 is constructed in the following manner. A single pulse cycle is utilized at a cuff pressure lower than the patient's measured diastolic pressure. The apex point 202 of the cycle is then set at the patient's measured systolic pressure. In the instant example, this is 140 mm Hg. The lowest point of the cycle, nadir point 204, is then set at the patient's measured diastolic pressure. In the instant example, this is 85 mm Hg. Using these two known points, the graph is then calibrated by linearly interpolating arterial pressures between the measured systolic pressure and the measured diastolic pressure on the graph to create a linear scale of arterial pressures.

The mean arterial pressure should be less than the patient's systolic pressure, and greater than his diastolic pressure. A pressure determination (deflection) point 206 is chosen because it meets the following criteria: first, when measuring mean arterial pressure, the pressure determination point is a point on the curve 200 wherein the patient's arterial pressure is decreasing with time. In other words, the pressure determination point 206 will be somewhere between the pulse maxima (apex point 202) and pulse minima (nadir point 204) and not at a point between the pulse minima (nadir point 204) and the pulse maxima of a succeeding cycle.

The second criteria met by pressure determination point 206 is that it represents a point wherein the rate of change of arterial pressure versus time changes significantly. When viewing the graph, this change is represented by a change in the slope of curve 200, wherein the slope of the curve 200 increases significantly. As shown in FIG. 6, the slope of the portion of curve 200 between apex point 202 and pressure determination point 206 is approximately minus 225 mm Hg. per second, whereas the slope of the portion of curve 200 in the interval between pressure determination point 206 and nadir point 204 is approximately minus 40 mm Hg. per second. Thus, it will be noticed that between pressure determination point 206 and nadir point 204, the slope of curve 200 increases significantly, although still remaining negative. Although the slope of the portion of the curve between the pressure determination point 206 and the nadir point 204 remains negative, the applicant has found that occasionally the slope of the curve will become positive for a short interval of this portion, such as between pressure determination point 206 and the two or three points which follow pressure determination point 206. It will be appreciated by those familiar with calculus that pressure determination point 206 can also be described as a point wherein the first derivative of curve 200 changes significantly or a point wherein the rate of change in the slope of curve 200 reaches a maximum in the interval between apex point 202 and nadir point 204.

The applicant has found that the use of a "deflection point," such as point 206, as a pressure determination point, yields quite consistent results in the measurement of the patient's mean arterial pressure. One experiment utilized by applicant to prove the consistency of this mathematical calculation method as an accurate and consistent determinor of mean arterial pressure is shown in FIGS. 6a and 6b.

Figure 6A:
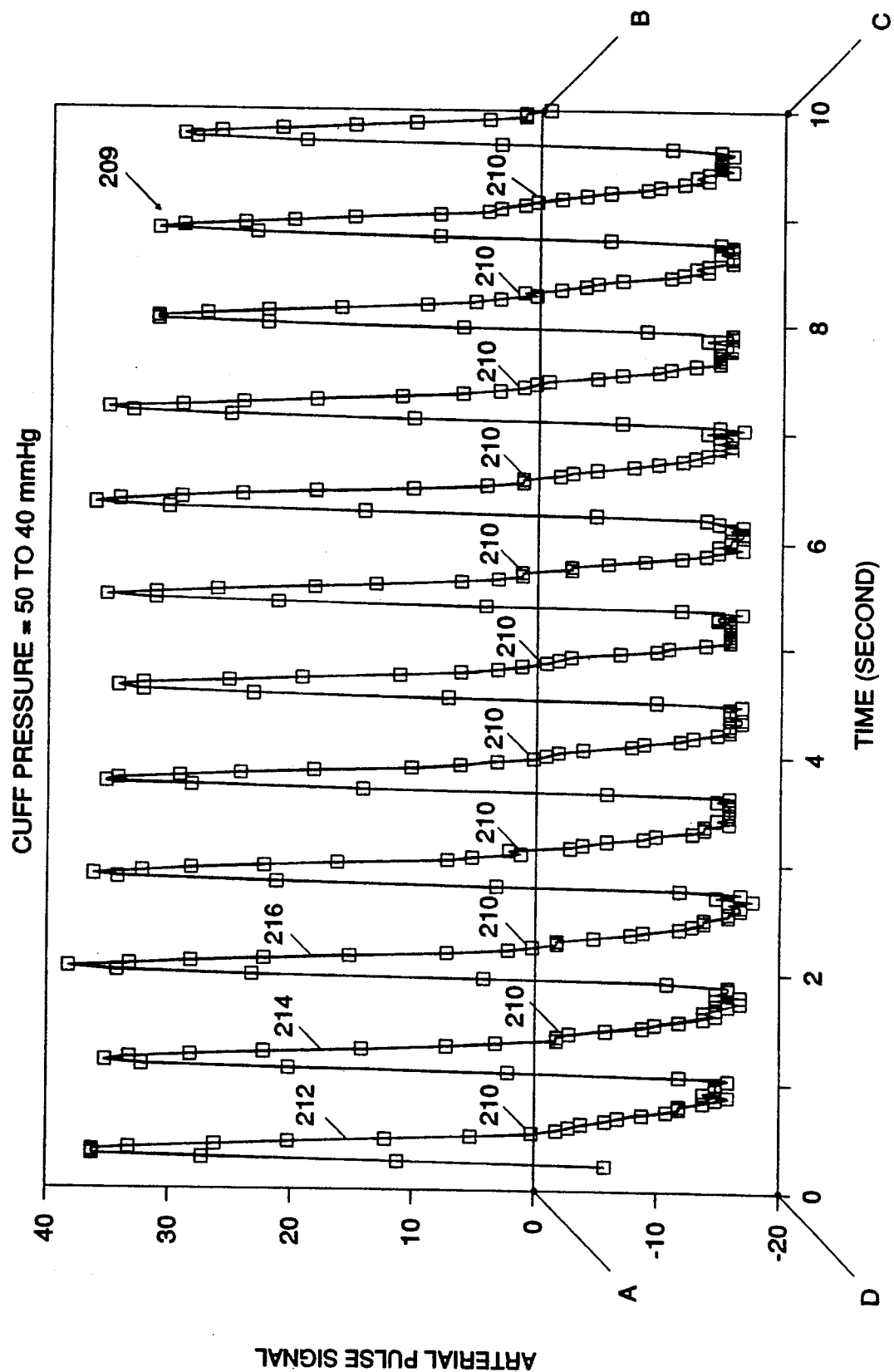
FIG. 6a is a graphic display illustrating the invention in its third mode of operation, wherein a plurality of pulse signals over a ten second time period are displayed.

FIG. 6a shows a series of pulse cycles shown on a graph wherein arterial pulse signal is shown as a function of time. In the graphs of FIGS. 6a and 6b, the arterial pulse signal equals zero (Y=0) line, is set to equal the mathematical true mean value of all pulsation signals displayed on the respective graphs. Another way of expressing this is that the area under entire curve 209 (FIG. 6a) equals the area of a rectangle defined by points A, B, C and D, which of course equals the area of the graph under the Y=0 line.

FIG. 6a shows a curve 209 of twelve pulse cycles recorded over a period of approximately ten seconds at a cuff pressure between 50 and 40 mm Hg., a cuff pressure less than a typical patient's diastolic pressure. It will be noticed that the pressure determining deflection points 210 of each cycle tend to hover around the Y=0 line, thus proving that the deflection point does accurately reflect the mean arterial pressure of the patient.

FIG. 6b is an expanded view of the first three cycles 212, 214, 216 shown in FIG. 6a. This expanded view illustrates more clearly that pressure determining deflection points correlate well between each other around the Y=0 line, and are not easily affected by other unknown oscillation noises. This fact is important in that it enables the present invention to provide a more precise method of determining mean arterial pressure than other known methods.

It should be noted that the precision by which the mathematical calculation method of the present invention determines mean arterial pressure is dependent upon an accurate determination of both systolic and diastolic pressures. This accurate determination is provided by the present invention and is described in conjunction with FIGS. 3 and 4 above.

The applicant has found that the mean arterial pressure is best measured at a cuff pressure less than the patient's diastolic pressure. At a pressure less than the patient's diastolic pressure, the cuff 10 and transducer 16 are utilized primarily as sensing devices to pick up the pulsation signal of the patient's arteries. When using a pressure-sensing or pulsation sensing device, such as an ultrasonic or optical transducer to pick up and record the arterial pulse signals, it is expected that one will achieve the same correlations between the pressure determination deflection point, the apex point, and the nadir point as are achieved through the use of a cuff 10 device. The similarity of these correlations permits a cuffless blood pressure measuring device to be utilized to provide accurate determinations of the patient's mean arterial pressure, so long as the patient's systolic and diastolic pressures are obtained by relatively accurate measuring devices.

Another feature of the present invention is that if the practitioner has knowledge of the manner in which the mean arterial deflection point, the systolic maximum apex point and the diastolic minimum nadir point are correlated, it is possible for the practitioner to determine any of the three points by knowing only two of the points. For example, if one obtains a patient's arterial pulse signal, diastolic pressure and mean arterial pressure, the practitioner can then calculate the patient's systolic pressure.

The determination of the patient's mean arterial pressure is a very important for enabling the practitioner to treat the patient properly. As discussed above, the patient's mean arterial pressure is generally equal to the patient's cardiac output times the total peripheral resistance of the patient's cardiovascular circulatory system. In controlling a patient's hypertension, the practitioner can choose either to control the patient's cardiac output by prescribing one type of medicine, or controlling the patient's total peripheral resistance by prescribing another type of medicine. It is important for a practitioner prescribing such medicine to have an accurate reading of the patient's mean arterial pressure to determine the correct dosages of such medicine to administer.

4. Fourth Mode.

Figure 7:
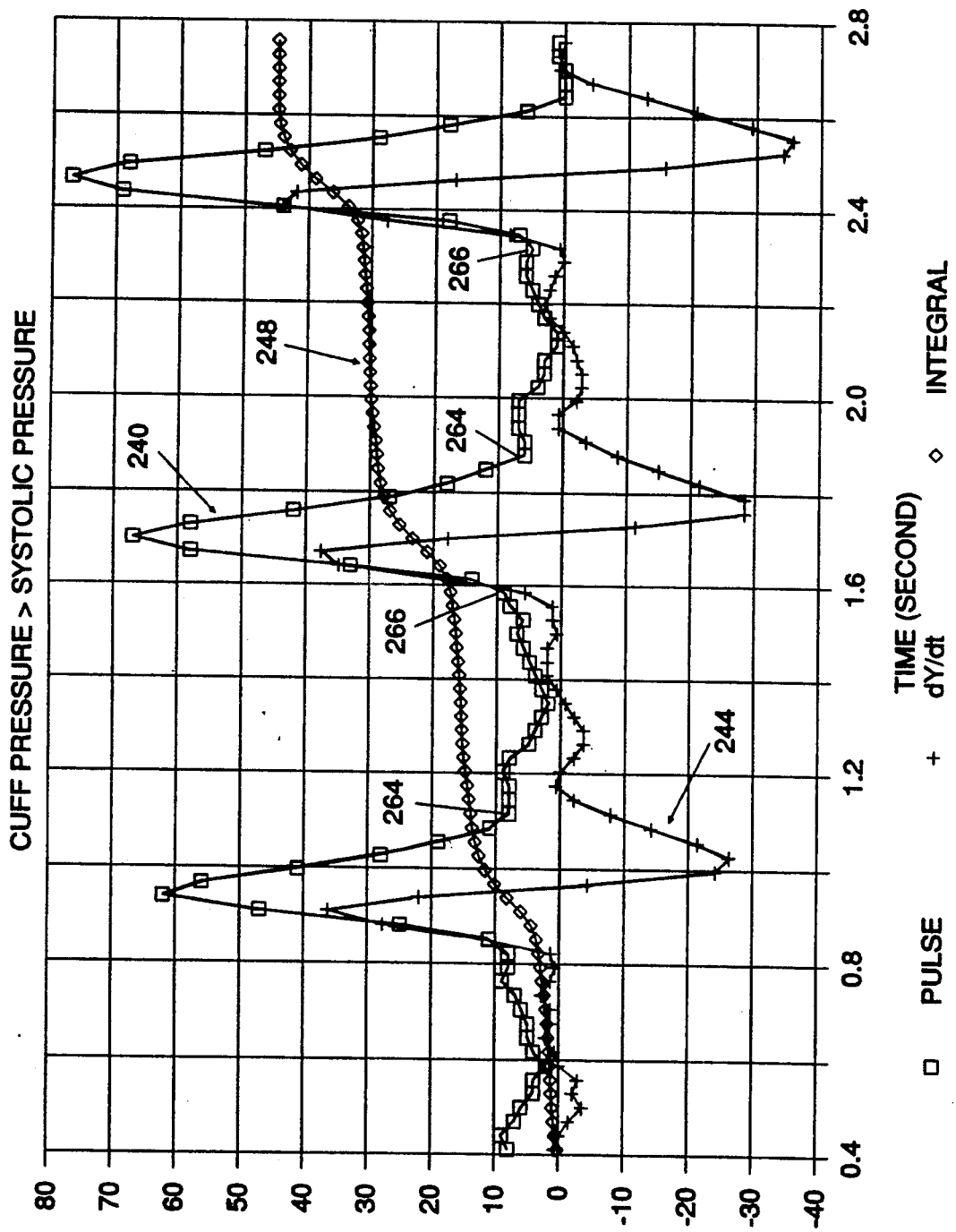
FIG. 7 is a graphic display showing information processed according to the present invention in its fourth mode, wherein pulse signal is displayed as a function of time, and wherein the original pulse signal, its first derivative signal and its integration signal are displayed in a range wherein cuff pressure is greater than the systolic pressure of FIG. 3.

FIG. 7 comprises a graphic display showing the present invention's fourth mode wherein data relating to arterial pulse wave forms is displayed as a function of time. The primary purpose of the fourth mode is to gather information about the condition of the patient's cardiovascular system, rather than determining the patient's blood pressure. Three curves are drawn on FIGS. 7 and 7a.

In FIG. 7, the first curve 240 comprises a series of data points connected together by the curve 240. The data points correspond to a arterial pressure pulse signal which, in the instant example, is measured at a cuff pressure greater than the patient's systolic pressure. The second curve, first derivative curve 244, is a curve comprising the first derivative of the arterial pulse signal curve 240. The third curve 248 comprises the integration of the arterial pressure pulse signal curve 240 over the duration of the portion of curve 240 shown in the graph.

Figure 7A:
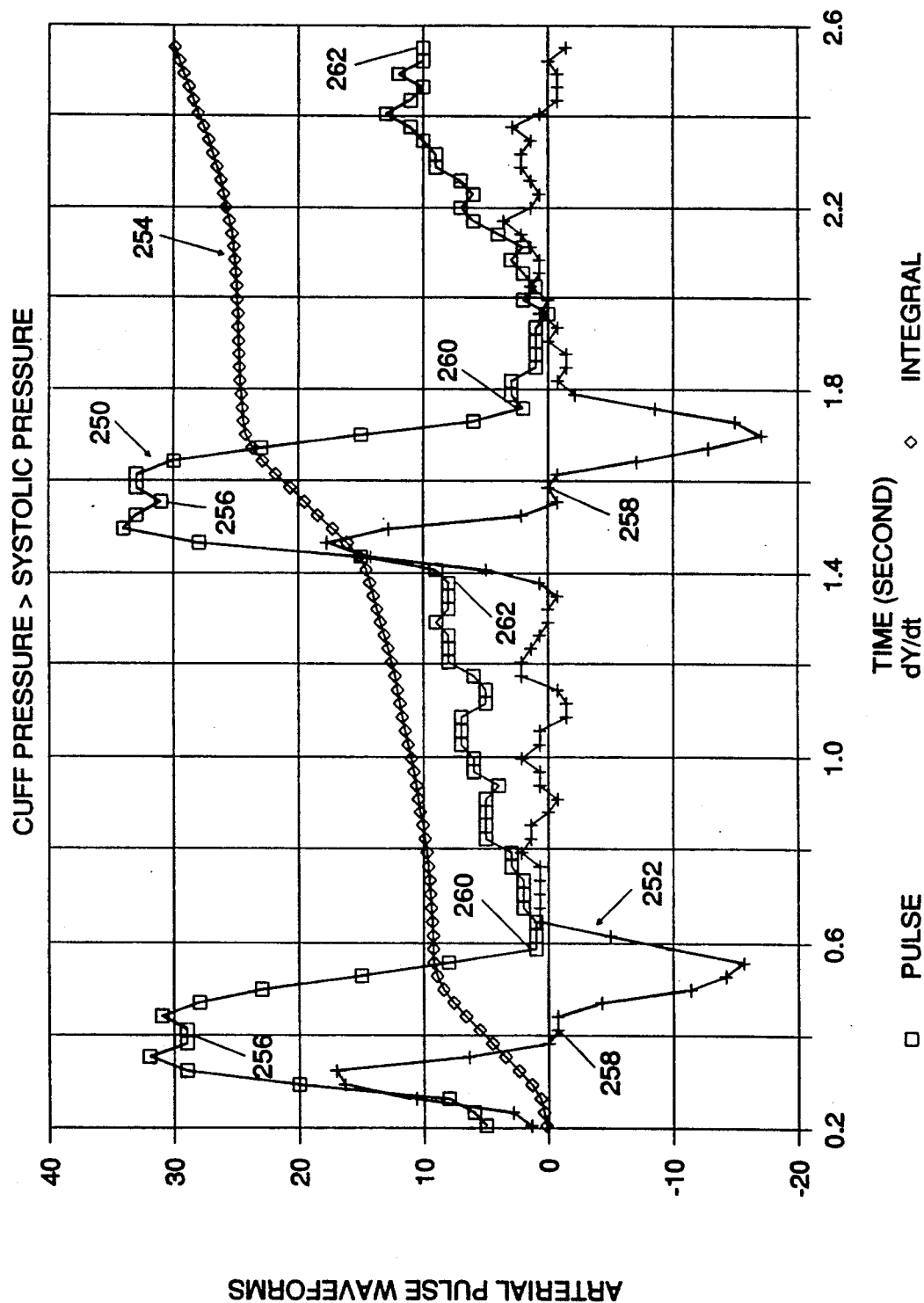
FIG. 7a is a display, similar to FIG. 7, showing the pulse signals of a male person exhibiting hypertension.

FIG. 7a contains three similar curves including an arterial pressure pulse signal curve 250, a derivative curve 252 which is the first derivative of arterial pressure curve 250, and an integration curve 254 which is an integration of the arterial pressure curve 250. FIG. 7 displays arterial pulse wave forms for a person with a normal cardiovascular condition, whereas FIG. 7a displays arterial pulse wave forms of a patient exhibiting hypertension. The patient whose arterial pulse wave forms are shown in FIG. 7a was found to have a measured systolic pressure of 158 mm Hg, a diastolic pressure of 80 mm Hg, and a mean arterial pressure of 105 mm Hg. As will be appreciated by those skilled in the medical art, a systolic pressure of 158 mm Hg is above normal.

It should also be noted that although the information shown in FIGS. 7 and 7a were obtained during a "test" wherein the cuff pressure was decreasing over time, this need not be the case. It is possible to obtain the information needed for the inventions, fourth and fifth mode by maintaining a constant cuff pressure.

Comparing FIGS. 7 and 7a, one will note that several differences exist between curves 240, 244, 248 and curves 250, 252, 254. These differences are indicative of the hypertensive condition of the patient of FIG. 7a. The first difference between the two sets of curves is that the curves 250, 252, 254 of the hypertensive patient (FIGS. 7a) are noisier than the curves 240, 244, 248 of the normal patient (FIG. 7). A second difference between the two sets of curves is that the arterial pressure pulse curve 250 of the hypertensive patient includes splits or dips such as at 256. These splits or dips 256 are absent in the arterial pulse pressure signal curve 240 of the normal patient. These splits or dips 256 are also reflected in the first derivative curve 252 of the hypertensive patient as deflection points 258 in the first derivative curve 252. The third difference between the two curves is that in the arterial pulse curve 250 of the hypertensive patient, the "diastolic" portion of the curve in each cycle from data point 260 to data point 262 rises to a higher level than the corresponding diastolic portion (from point 264 to point 266) of the arterial pulse curve 240 of the normal patient.

Several reasons exist for utilizing arterial pulse curves which are taken at a cuff pressure above the patient's systolic pressure. One reason for using a suprasystolic cuff pressure is that when the cuff pressure is greater than the systolic pressure, the patient's arterial vessels in the arm are blocked at the cuff 10 location. With such blockage, the blood vessels work as a signal transfer line which transmit pressure signals from the heart to the aorta, and through the arterial blood vessels to the cuff 10, which then picks up the vibration signals. Although a vessel filled with blood is not a perfect vibration-conducting medium, the information so obtained should be qualitatively representative of the aorta pressure curve, which heretofore could only be measured by invasive blood pressure determining means. Additionally, the information so obtained should also reflect other influences such as the characteristics of the arterial vessels and the cuff 10-to-blood-vessel coupling effects.

Although an interpretation of the wave forms shown in FIGS. 7 and 7a is very difficult, the wave forms of FIGS. 7 and 7a are useful to the practitioner when compared to similar prior data from the same patient. When compared to such a prior data, the information of FIGS. 7 and 7a can provide the practitioner with important information about the condition of the patient's cardiovascular system, such as the deterioration of the patient's heart, aortic valve noises, and changes in blood flow due to changes in the patient's blood vessels.

Additional information is provided by the first derivative curves 244, 252. The first derivative curves 244, 252 display the change of slope of arterial pressure curves 240, 250, respectively. As such, the first derivative curves 244, 252 are generally more sensitive to the presence of low level noises. A display of these low level noises can be used by the practitioner to help better diagnose noises associated with certain cardiovascular problems. For example, in FIG. 7a many of the small oscillation noises present in the arterial pulse pressure curve 250 are better displayed on the first derivative curve 252. Examples of these small oscillations are splits 256 which are better displayed as deflection points 258 on the first derivative curve 252.

The integration pressure curves 248, 254 are the summation of the pressure signal data form the data collected at the beginning (left) of the graph to the last point collected and displayed on the graph. Thus, the information displayed by the integration curves 248, 254 relates to the total accumulated arterial pressure multiplied by time over the course of the display. Since the information displayed in FIGS. 7 and 7a was obtained at suprasystolic pressures, no blood flowed through the body part in area of the cuff 10. The integration of each pulse therefore provides information about the strength of each stroke of the heart. Although the integration curves 248, 254 are difficult to interpret by themselves, they are useful to the practitioner when used in conjunction with similar integration curves taken from the patient at an earlier date, to provide information to the practitioner about the condition of the patient's cardiovascular system.

5. Fifth Mode.

Figure 8:
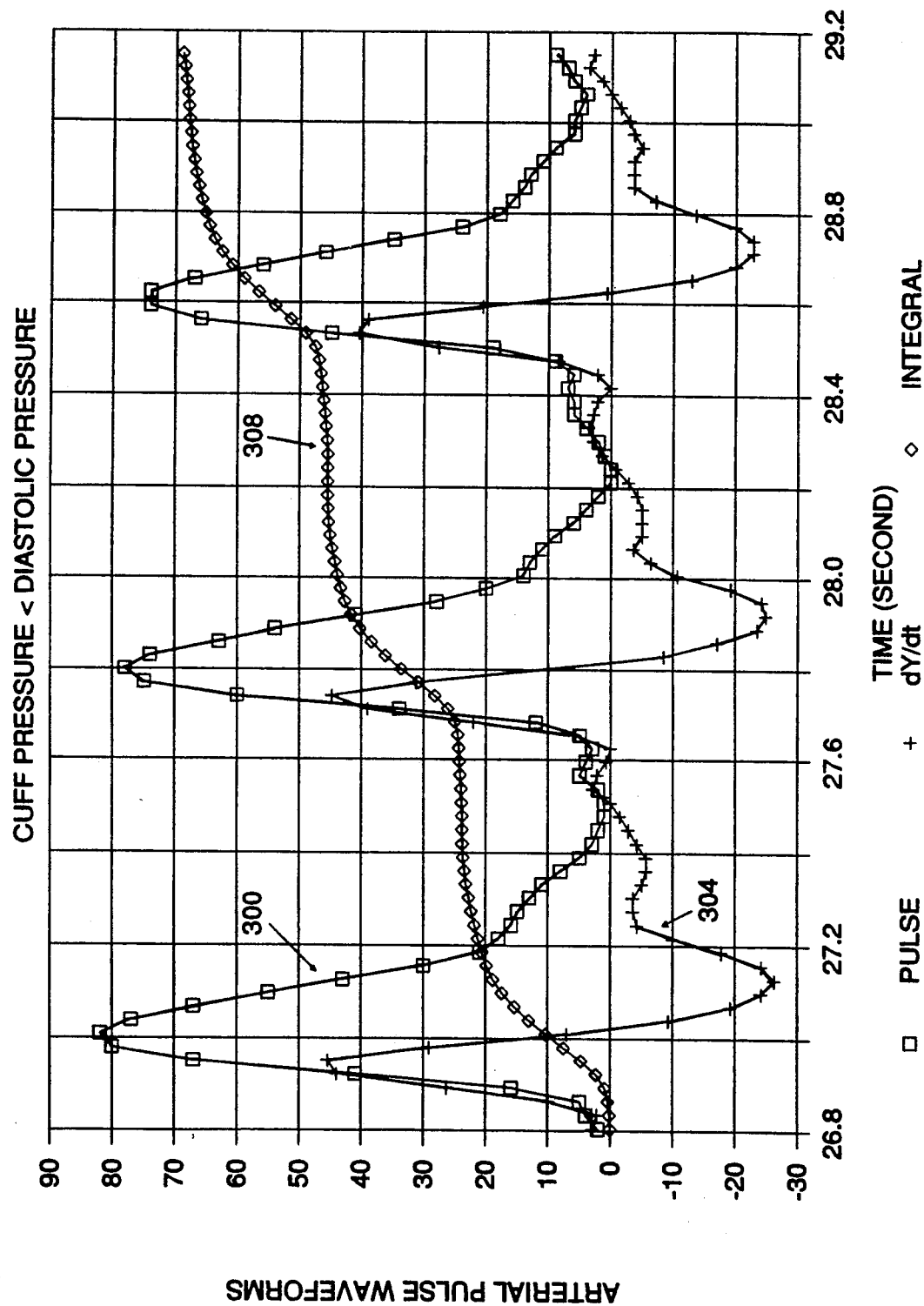
FIG. 8 is a display showing information processed according to the present invention in its fifth mode, wherein pulse signal is displayed as a function of time, and wherein the original pulse signal, its first derivative signal and its integration signal are displayed in a range wherein cuff pressure is less than the diastolic pressure of FIG. 5.
Figure 8A:
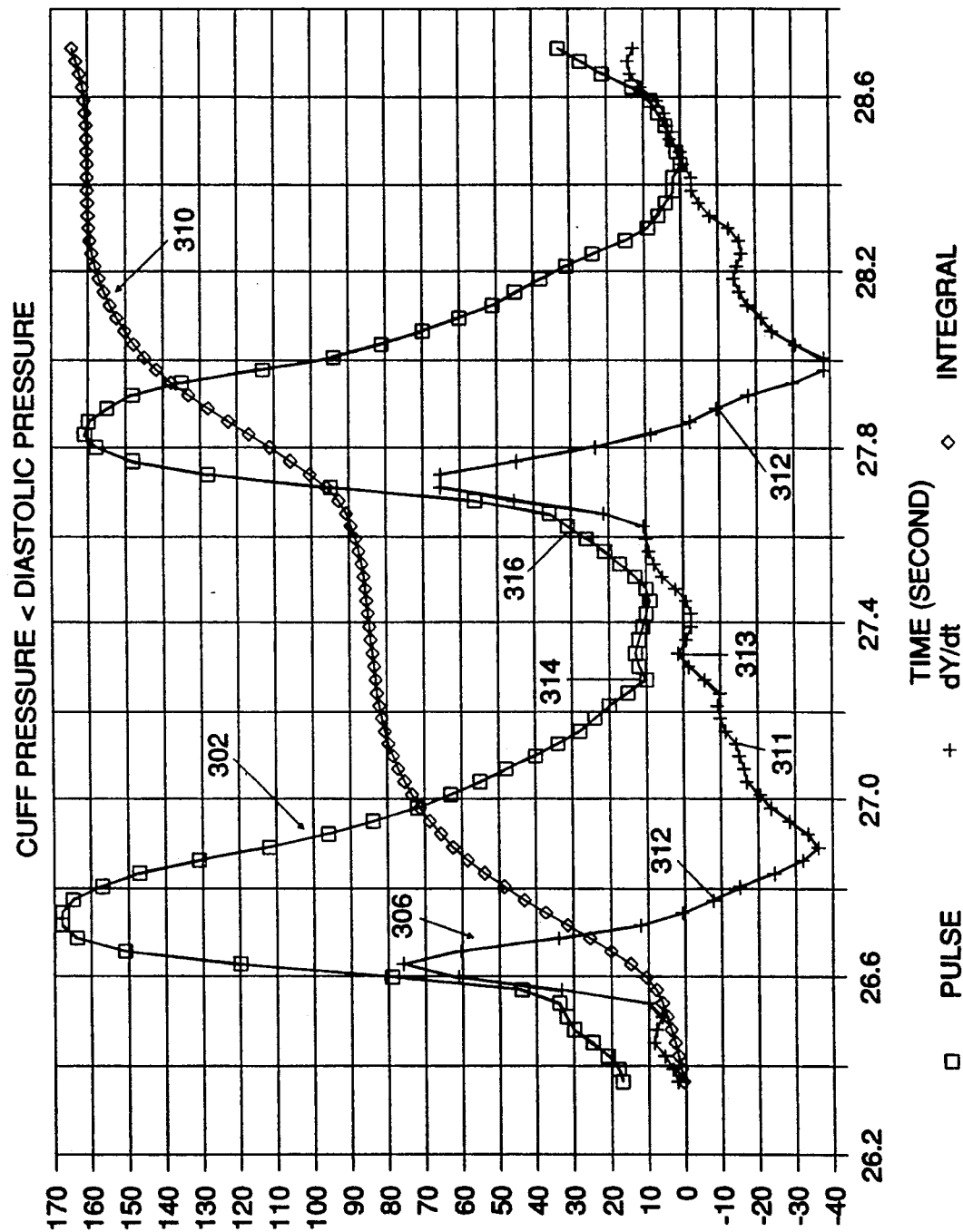
FIG. 8a is a graphic display, similar to FIG. 8, showing the pulse signals of a male person exhibiting hypertension.

The graphic displays shown in FIGS. 8 and 8a set forth data presented by the invention in its fifth mode. FIGS. 8 and 8a are similar to FIGS. 7 and 7a in that both sets of figures show arterial pulse wave forms as a function of time, and are utilized primarily to provide information about the condition of the patient's cardiovascular condition rather than for determining blood pressure.

Additionally, both sets of figures contain three curves. FIGS. 8 and 8a each include arterial pressure pulse curves 300, 302, first derivative curves 304, 306, and integration curves 308, 310. The primary difference between FIGS. 7 and 7a and FIGS. 8 and 8a is the FIGS. 7 and 7a display information obtained at suprasystolic cuff pressures, whereas FIGS. 8 and 8a display information obtained at subdiastolic cuff pressures.

FIG. 8 presents information taken from a male patient having normal blood pressure, and FIG. 8a presents information taken from a male person exhibiting hypertension. Several major differences exist between the curves 300, 304, 308 of the normal person (FIG. 8) and the curves 302, 306, 310 of the hypertensive person (FIG. 8a). First, it will be noticed that more high frequency noises are present on the arterial pulse pressure curve 302 of the hypertensive patient. Examples of such high frequency noises are best shown at points 311, 313 of the first derivative curve 306 of FIG. 8a.

A second difference is the presence of "splits" at the apex of the arterial pulse pressure curve 302 of the hypertensive patient. Although no splits are visible on the arterial pulse pressure curve 302 of the hypertensive patient, deflection points 312 on the first derivative curve clearly indicate the presence of such splits. A third difference is that the hypertensive curve exhibits significant increases in the diastolic portion of the curve, between points 314, 316, similar to the significant increase shown in the diastolic portions of the arterial pulse curve 250 between points 260 and 262 of FIG. 7a.

The information displayed in the fifth mode is similar to the information displayed in the fourth mode of the present invention. The primary difference between the information displayed results from the fact that in the fourth mode (FIGS. 7 and 7a) the cuff pressure at which the information is taken is at a suprasystolic pressure. Therefore, in the fourth mode, no blood is flowing past the cuff 10 picking up the signals. In the fifth mode, however, the restrictions on the flow of blood caused by the cuff 10 are minimal so that blood can flow through the area freely.

Theoretically, in the fourth mode (above systolic pressure) with no blood flowing, the cuff 10 measures the strength of the heart stroke which sends out a pressure signal to the cuff 10, whereas in the fifth mode (below diastolic pressure) the cuff 10 measures the oscillations of the arterial circulation system caused by the pressure wave emanating from the heart stroke on the arm where the cuff 10 is placed. Generally, therefore, the fourth mode, with no blood flowing, provides information about the strength of the heart contraction. The fifth mode, with the blood flowing without restriction, gives information to the practitioner about the flow of blood in the circulatory system. Information about the strength of the heart and the amount of blood flow in the cardiovascular system relate directly to the cardiac output and the resistance of the cardiovascular circulatory system respectively. As discussed above, information about cardiac output and the resistance of the cardiovascular system are essential to the practitioner in the diagnosis and treatment of patients having hypertension.

6. Sixth Mode.

The sixth mode in which the invention can be used relates to the use of the method and apparatus of the present invention in conjunction with the tuning of a cardiac pacemaker.

Two primary types of pacemakers exist, fixed rate pacemakers and cardiac responsive pacemakers. A fixed rate pacemaker is a pacemaker that transmits an electrical impulse at a steady rate regardless of the patient's own cardiac impulses. Because such pacing interferes with normal cardiac activity, fixed rate pacemakers are rarely used.

The far more commonly used pacemaker is a heart responsive pacemaker. A heart responsive pacemaker is one wherein the firing sequence of the pacemaker is determined by a particular heart activity. Typically, these heart responsive pacemakers include a sensing electrode which can sense a heart electrical activity such as an R-wave or atrial depolarization. The heart responsive pacemaker is designed to initiate a firing sequence after an appropriate delay from the sensed heart electrical activity. As used in this application, "firing sequence" refers to both the amount of time which constitutes the delay between the sensed heart electrical activity, and the time at which the pacemaker transmits an electrical impulse to the heart or heart chamber. Additionally, the term firing sequence also includes the rate (usually expressed as beats per minute) at which these electrical impulses are transmitted to the heart.

Heart responsive pacemakers can be either dual chamber pacemakers or single chamber pacemakers A dual chamber pacemaker contains a pair of electrodes to stimulate two heart chambers, such as the right atrium and right ventricle. A single chamber pacemaker stimulates only one of the heart's four chambers.

One of the jobs of a cardiologist installing a pacemaker is to establish a proper firing sequence for the pacemaker. To perform this, the doctor usually works in conjunction with a pacemaker engineer, as the pacemaker engineer has the proper tools and training to adjust the firing sequence of the pacemaker. A proper firing sequence is usually established in the following manner.

A patient is first hooked up to both an electrocardiograph (EKG) and the applicant's invention. The pacemaker engineer and doctor first use the EKG to either lengthen or shorten the time between the sensed heart electrical activity and the transmission of an impulse, so that the patient's EKG closely approximates a "normal" EKG. If the doctor determines that the patient's EKG is abnormal, he will instruct the pacemaker engineer to either shorten or lengthen the firing sequence, as appropriate.

When establishing a proper firing sequence for a dual chamber pacemaker, the pacemaker engineer and doctor will usually first establish the proper firing sequence of the pacemaker electrode which stimulates the ventricle. This procedure is known as "tuning the ventricle". After the ventricle is properly tuned, the pacemaker engineer and doctor will then establish a proper firing sequence for the electrode which stimulates the atrium ("tuning the atrium"). Preferably, the atrium and ventricle are tuned together, to ensure that the relative firing sequences of the two are complimentary, and to ensure that the patient's EKG approximates a normal EKG. Often, the pacemaker engineer will make adjustments to the tuning of the atrium and ventricle to finely tune the atrium firing sequence or ventricle firing sequence, to optimize the proper relative firing sequences of the atrium and ventricle. In current practice, doctors will usually use a conventional non-invasive blood measuring device to determine and record the patient's blood pressure. However, it is believed that the blood pressure monitoring device is not used to tune the pacemaker.

Even though the patient's EKG may approximate a normal EKG, it has been found by the applicant that the indicated normalcy of the EKG does not always mean that the pacemaker is properly tuned to optimize the patient's hemodynamics. The present invention enables the physician to finely tune the firing sequence to optimize the patient's hemodynamics in the following manner.

After the doctor and pacemaker engineer have tuned the firing sequence of the pacemaker as well as possible using the EKG, the device of the applicant's invention is used by the doctor and engineer in a manner similar to that described above in connection with the applicant's method of determining the patient's blood pressure. The pressure induced by the pressure inducing means is elevated to a suprasystolic pressure. The pressure induced by the pressure inducing means is then decreased over time to a subdiastolic pressure. The transducer is used to obtain a data stream which includes pressure data and pulsation signal data. A graphic display means such as a video display monitor, or graphic printout is used to display the information stream. Preferably, the information stream is displayed as pulsation signal data as a function of cuff pressure data over a range from a suprasystolic pressure to a subdiastolic pressure. An example of such a graphic display is shown in FIG. 2. It will be noticed that the graphic display of FIG. 2 comprises a generally sinusoidal information stream curve containing a series of apex points, such as apex points 54, 56, 61, 60 and 62, and a series of nadir points such as nadir points 58, 67 and 64.

FIG. 2 shows a pulse signal vs. cuff pressure curve of a person having a normal, healthy cardiovascular condition. Several characteristics are shown in FIG. 2 which indicate that the patient's condition is normal and healthy. One characteristic relates to the shape of the pulse signal curve. If one were to create a curve by drawing a line which connected adjacent apex points (such as by drawing a line between apex points 54 and 56), and were to draw a second line which connected adjacent nadir points, one would create a pair of generally smoothly ascending and descending bell-shaped curves. The line which connected adjacent apex points would be, to some extent, a mirror image of the line which connected adjacent nadir points. The line connecting adjacent apex points would rise smoothly, and reach its apex at peak apex point 61. As the line continued to the right along the cuff pressure axis, it would descend gradually toward the end of the graph. The line connecting adjacent nadir points would descend relatively smoothly, until it reached its lowest most point at the nadir point to the left of nadir point 67. The curve would then rise relatively smoothly to the end of the graph.

Another characteristic illustrating that the patient's cardiovascular condition is in an acceptable, healthy range, is that the patient's systolic, diastolic and mean arterial pressures are in a normal range. As shown in FIG. 3, the patient's systolic pressure is about 140.0 mm Hg. As shown in FIG. 5, the patient's diastolic pressure is about 85 mm Hg. As shown in FIGS. 3 and 6, the patient's mean arterial pressure is about 93 mm Hg.

A graph of pulse signal vs. cuff pressure information is shown in FIG. 11. The patient for whom the information was taken was a patient in whom a heart responsive, dual chamber, right atrium and right ventricle pacemaker was being installed. However, during the time in which the information stream of FIG. 11 was taken, only the right ventricle electrode was being fired. The doctor and pacemaker engineer finely tuned this patient's right ventricle as well as they were able with an EKG. The apparatus of the present invention was then activated and the information stream shown in FIG. 11 was generated using the method of the present invention.

When the information stream of FIG. 11, is compared to the information stream of FIG. 2, it will be noticed that the graphic displays are substantially different. The lines 402, 404 in FIG. 11 the adjacent apex points and nadir points, respectively, do not approximate a smooth bell curve about the cuff pressure axis. Rather, the relative increase or decrease in arterial pulse signals between adjacent points appears to be rather irregular. Although the information stream shown in FIG. 2 also contains irregularities, it will be noticed that the degree of irregularity of the information stream shown in FIG. 11 far exceeds the irregularity shown in FIG. 2. Although the irregularity displayed by the information stream of FIG. 2 can be attributed to artifacts in the data, or aspiration by the patient, the high degree of irregularity shown in FIG. 11 rules out such artifacts or aspiration as the cause of the irregularities.

By examining the information stream shown in FIG. 11, and comparing it to a normal information stream (e.g. FIG 2) the doctor can better determine whether the firing sequence of the pacemaker is correct. The high degree of irregularity indicates to the doctor and pacemaker engineer that the firing sequence, or some other characteristic of the pacemaker is not correctly adjusted. For example, the abnormality shown in FIG. 11 may indicate that the pacemaker engineer did not properly establish the timing or sensing of the R-wave or arterial depolarization signal. Another possibility is that the doctor and pacemaker engineer did not adjust the firing sequence correctly. A third problem that may be causing the irregularity is that one or both electrodes may be mis-positioned in the heart.

An unexpected phenomena was observed during the generation of the information stream on FIG. 11. Using the present invention, the patient's blood pressure was measured as systolic: 120, diastolic: 75, mean arterial: 90. The irregularity of the signal appeared to induce error in a conventional non-invasive blood pressure measuring device used in tandem with the applicant's invention. This conventional blood pressure device reported that the same patient's blood pressures were systolic: 149, diastolic: 60, and mean arterial: 109.

In response to the irregularities shown in FIG. 11, the doctor and pacemaker engineer should reconnect the patient to the electrocardiograph, and re-tune the pacemaker or reposition the electrodes to establish a more regular arterial pulse signal, and hence better tune the pacemaker to the patient's hemodynamics. The procedure of tuning the pacemaker and then using the instant invention to detect irregularities in the patient's arterial pulse signal is repeated as often as necessary to minimize the cardiovascular irregularities displayed in the information stream.

FIG. 12 shows a graphic display of the patient's arterial pulse signal that is graphed as a function of cuff pressure for the same patient during the time when only the pacemaker's right atrium electrode was transmitting impulses. The graphic display of FIG. 12 exhibits a different set of irregularities than that shown in FIG. 11.

It will be noticed that if one were to draw a line connecting adjacent apex points, such as apex points 410, 412 and 414, and to draw a second line connecting adjacent nadir points, such as nadir points 416, 418, 420, and 422, the two resultant lines would approximate a normal, bell shaped curve. Notwithstanding the seemingly normal appearance, it will be noticed from the graph that the patient's systolic blood pressure, as determined form nadir point 422, is approximately 155 mm Hg. As will be appreciated, this systolic pressure far exceeds the normal range of systolic blood pressures, and represents an unhealthy blood pressure situation.

This abnormally high systolic pressure may indicate that the right atrium is pumping too much blood for the remainder of the heart to properly handle. One possible solution for this problem is for the cardiologist to install a dual chamber pacemaker to stimulate another chamber in the heart. This second chamber so stimulated will then be capable of pumping this additional blood being fed to it by the stimulated right atrium. This dual chamber stimulation will likely result in the volumes being pumped by the four chambers of the heart being more "in balance", and the pumping cycle of the heart being more in tune with the natural rhythm of the heart.

A graphic display of an arterial pulse signal which represents a patient having a dual chamber, heart responsive pacemaker in shown in FIG. 13. The particular pacemaker used to generate the information stream of FIG. 13 was one which stimulated both the right ventricle and the right atrium. FIG. 13 also shows an information stream which represents a pacemaker finely tuned to an acceptable condition, for the same patient whose information streams are shown in FIGS. 11 and 12 as being unacceptable.

It will be noticed that a line drawn between adjacent apex points, such as apex points 428, 430, 432 and 434, and a line drawn between adjacent nadir points, such as nadir points 438, 440, 442 and 446 would produce a pair of generally bell shaped curves about the axis of cuff pressure. Admittedly, the bell shaped curves produced from the information stream of graph 11 are not as symmetrical as the bell shaped a curves produced from the information stream of FIG. 2. However, it must be remembered that the information stream shown in FIG. 13 represents an acceptable absence of irregularities in view of the fact that the patient's heart is probably in a substandard condition. Additionally, it will be noticed from the information stream displayed in FIG. 13 that the patient's systolic pressure is at about 130 mm Hg., the patient's diastolic pressure is at about 65 mm Hg, and his mean arterial pressure is about 80 mm Hg. Thus, the patient's blood pressures are also within an acceptable range. A condition such as that shown in graph 13 indicates to the physician and the pacemaker engineer that the pacemaker is well tuned for that particular patient, and that the firing sequence established by the pacemaker is acceptable.

The present invention also has utility in enabling the physician to monitor the pacemaker's performance after the installation. The amount, type, and accuracy of the information presented by the present invention will enable the physician to determine whether the pacemaker is performing properly when the physician examines the patient during routine check-ups.

Although the invention has been described in detail with reference to the illustrated preferred embodiments, variations and modifications exist within the scope and spirit of the invention as described and as defined in the following claims:

What is claimed is:

1. A method of tuning a heart pacemaker comprising the steps of
    (a) using an electrocardiographic device to adjust the firing sequence of the pacemaker,
    (b) affixing a non-invasive pressure inducing means and transducer means to the patient,
    (c) elevating the pressure induced by the pressure inducing means to a suprasystolic pressure,
    (d) decreasing the pressure induced by the pressure inducing means over time to a subdiastolic pressure,
    (e) obtaining a data stream from the transducer means, the data stream including pressure data and pulsation signal data,
    (f) examining the information stream to detect cardiovascular irregularities displayed in the information stream, and
    (g) repeating steps (e) to (f), if necessary, to minimize the cardiovascular irregularities displayed in the information stream.

2. The method of claim 1 further comprising the steps of providing a graphic display means, and graphically displaying the information stream, as pulsation signal data as a function of cuff pressure data over a range from a suprasystolic pressure to a subdiastolic pressure to create a generally sinusoidal information stream curve containing a series of apex points and a series of nadir points.

3. The method of claim 2 wherein the step of examining the information stream comprises the step of examining the information stream curve to determine whether at least one of the series of apex points and nadir points forms a generally smoothly ascending and descending bell shaped curve relative to a graphic axis of cuff pressure.

4. The method of 2 wherein the step of examining the information stream comprises the step of examining the information stream curve to determine at least one of the patient's systolic, diasolic and mean arterial blood pressure, to determine whether said at least one of the patient's systolic, diastolic and mean arterial blood pressure falls outside of a physiologically acceptable range.

* * * * *